US012567480B2

(12) United States Patent
Sadeh et al.

(10) Patent No.: US 12,567,480 B2
(45) Date of Patent: Mar. 3, 2026

(54) DEEP LEARNING MODEL FOR PREDICTING TUMOR-SPECIFIC NEOANTIGEN MHC CLASS I OR CLASS II IMMUNOGENICITY

(71) Applicant: AMAZON TECHNOLOGIES, INC., Reno, NV (US)

(72) Inventors: Gil Sadeh, Herzliya (IL); David Heckerman, Bellevue, WA (US); Layne Christopher Price, Seattle, WA (US); Frank Wilhelm Schmitz, Seattle, WA (US); Anta Imata Safo, Seattle, WA (US); Jasleen Kaur Grewal, Vancouver (CA)

(73) Assignee: AMAZON TECHNOLOGIES, INC., Reno, NV (US)

( * ) Notice: Subject to any disclaimer, the term of this patent is extended or adjusted under 35 U.S.C. 154(b) by 704 days.

(21) Appl. No.: 17/617,665

(22) PCT Filed: Dec. 1, 2021

(86) PCT No.: PCT/US2021/061399
§ 371 (c)(1),
(2) Date: Dec. 9, 2021

(87) PCT Pub. No.: WO2022/159176
PCT Pub. Date: Jul. 28, 2022

(65) Prior Publication Data
US 2023/0074591 A1 Mar. 9, 2023

Related U.S. Application Data

(60) Provisional application No. 63/139,074, filed on Jan. 19, 2021.

(51) Int. Cl.
| | |
|---|---|
| *G16B 20/20* | (2019.01) |
| *G06N 3/02* | (2006.01) |
| *G16B 20/30* | (2019.01) |

(52) U.S. Cl.
CPC ............... *G16B 20/20* (2019.02); *G06N 3/02* (2013.01); *G16B 20/30* (2019.02)

(58) Field of Classification Search
None
See application file for complete search history.

(56) References Cited

PUBLICATIONS

O'Donnell, Timothy J., et al: "MHCflurry 2.0: Improved Pan-Allele Prediction of MHC Class I-Presented Peptides by Incorporating Antigen Processing", Cell Systems, vol. 11, No. 1, Jul. 1, 2020 (Jul. 1, 2020), pp. 42-48.

*Primary Examiner* — Anna Skibinsky
(74) *Attorney, Agent, or Firm* — Hogan Lovells US LLP

(57) ABSTRACT

Disclosed herein are methods for predicting tumor-specific neoantigen MHC class I or MHC class II immunogenicity by jointly predicting MHC class I or MHC class II binding affinity and predicting the likelihood a tumor-specific neoantigen will be presented by a MHC class I or class II protein on a cell-surface.

21 Claims, No Drawings

DEEP LEARNING MODEL FOR PREDICTING TUMOR-SPECIFIC NEOANTIGEN MHC CLASS I OR CLASS II IMMUNOGENICITY

The present application is a U.S. National Phase Application of International Application No. PCT/US2021/061399, filed on Dec. 1, 2021, which claims the benefit of U.S. Provisional Application No. 63/139,074 filed on Jan. 19, 2021, each of which are incorporated herein by reference in their entirety.

REFERENCE TO A SEQUENCE LISTING

This application contains a Sequence Listing in computer readable form. The computer readable form is incorporated herein by reference. Said ASCII copy, created on Dec. 22, 2021, is named 146401_091568_SL.txt and is 1,545 bytes in size.

1. BACKGROUND

Cancer is a leading cause of death worldwide accounting for 1 in 4 of all deaths. Siegel et al., CA: A Cancer Journal for Clinicians, 68:7-30 (2018). There were 18.1 million new cancer cases and 9.6 million cancer-related deaths in 2018. Bray et al., CA: A Cancer Journal for Clinicians, 68(6):394-424. There are a number of existing standard of care cancer therapies, including ablation techniques (e.g., surgical procedures and radiation) and chemical techniques (e.g., chemotherapeutic agents). Unfortunately, such therapies are frequently associated with serious risk, toxic side effects, and extremely high costs, as well as uncertain efficacy.

Cancer immunotherapy (e.g., cancer vaccine) has emerged as a promising cancer treatment modality. The goal of cancer immunotherapy is to harness the immune system for selective destruction of cancer while leaving normal tissues unharmed. Traditional cancer vaccines typically target tumor-associated antigens. Tumor-associated antigens are typically present in normal tissues but overexpressed in cancer. However, because these antigens are often present in normal tissue immune tolerance can prevent immune activation. Several clinical trials targeting tumor-associated antigens have failed to demonstrate a durable beneficial effect compared to standard of care treatment. Li et al., Ann Oncol., 28 (Suppl 12): xii11-xii17 (2017).

Neoantigens represent an attractive target for cancer immunotherapies. Neoantigens are non-autologous proteins with individual specificity. Neoantigens are derived from random somatic mutations in the tumor cell genome and are not expressed on the surface of normal cells. Id. Because neoantigens are expressed exclusively on tumor cells, and thus do not induce central immune tolerance, cancer vaccines targeting cancer neoantigens have potential advantages, including decreased central immune tolerance and an improved safety profile. Id.

The mutational landscape of cancer is complex and tumor mutations are generally unique to each individual subject. Most somatic mutations detected by sequencing do not result in effective neoantigens. Only a small percentage of mutations in the tumor DNA, or a tumor cell, are transcribed, translated, and processed into a tumor-specific neoantigen with sufficient accuracy to design a vaccine that is likely to be effective. Further, not all neoantigens are immunogenic. In fact, the proportion of T cells spontaneously recognizing endogenous neoantigens is about 1% to 2%. See, Paul et al., J. Immunol., 192, 5831-5839 (2013);

Yewdell, Immunity, 25, 533-543 (2006). Of the approximately 1% of the neoantigens binding to MHC, only approximately 50% of the neoantigens will be recognized by a T cell, and only 30-40% will be naturally processed, enabling tumor cell killing. Id.

Current in silico methods largely focus only on modeling which neoantigen peptides bind to the MHC-I or MHC-II molecule or predicting which neoantigens will likely be processed by the tumor cell into short peptides and presented by MHC class I/II molecules. Available tools lack predictive accuracy to determine which of the presented peptides will be immunogenic. As such, existing methods are associated with a low positive predictive value. For example, in a study three melanoma patients were each immunized with seven peptides with in vitro-corroborated MHC-binding affinities <500 nM. Carreno et al., Science, 348, 803-808 (2015). Of the 21 peptides tested, only 9 induced a T-cell response. Id. If personalized vaccines containing neoantigen peptides are designed using methods with a low positive predictive value, patients are unlikely to receive a therapeutic neoantigen capable of eliciting an immune response against the cancer. Moreover, current technologies are time consuming and laborious.

Accordingly, the systematic identification of personalized neoantigens in cancer patients is a critical requisite for the success of developing personalized cancer vaccines. Thus, it remains a challenge to efficiently and accurately predict immunogenic neoantigen candidates that have a high positive predictive value for personalized vaccines.

2. SUMMARY

The disclosure relates to novel methods for predicting tumor-specific neoantigen MHC class I or MHC class II immunogenicity by jointly predicting MHC class I or MHC class II binding affinity and predicting the likelihood that the tumor-specific neoantigen will be presented by a MHC class I or MHC class II protein on a cell-surface. The method accurately identifies tumor-specific neoantigens with a high predictive value that are likely to be processed by the tumor cell into peptides that bind a subject's MHC class I or MHC class II molecules, and that will likely contact a T-cell receptor and ultimately be immunogenic. This method has a high predictive accuracy for identifying neoantigens that will elicit an immune response, which is critical for developing an effective personalized immunogenic composition (e.g., cancer vaccine). This has been a hurdle with existing approaches.

Moreover, the methods described herein outperform the gold-standard predictors, MHCflurry-1.4 binding affinity predictor, as well as the MHCflurry-2.0 predictor. See, Examples section for additional details. Each of these models are separate predictors. MHCflurry-1.4 is an allele-specific class I MHC binding predictor (O'Donnell et al., Cell System, 7:129-132 (2018)). The MHCflurry-2.0 predictor is a pan-allele predictor of MHC class I presented peptides.

The inventors additionally have developed an immunogenicity evaluation data set to create a unique benchmark, which directly evaluates the method's ability to retrieve immunogenic peptides from a large peptide candidate pool for given MHC class I alleles. This ability is an essential component for personalized immunotherapy-based vaccine design.

In order to more clearly describe the method for predicting tumor-specific neoantigen MHC class I immunogenicity FIG. 1 provides a schematic flow-diagram of the method.

The method for predicting tumor-specific neoantigen MHC class I or MHC class II immunogenicity begins with obtaining a peptide sequence for a tumor-specific neoantigen and the corresponding flanking regions of the peptide sequence. The flanking region can be an amino acid sequence directly to the left of the tumor-specific neoantigen peptide or directly to the right of the tumor-specific neoantigen peptide. For example, the flanking region can be an amino acid sequence that is on the C-terminus and/or the N-terminus of the tumor-specific neoantigen peptide. Typically, the flanking region can be about 10 amino acids in length. For example, the flanking region directly to the left of the tumor-specific neoantigen can be about 5 amino acids in length. For example, the flanking region directly to the right of the tumor-specific neoantigen can be about 5 amino acids in length. The peptide sequence and the flanking regions are then encoded into a numerical vector. Each numerical vector comprises amino acid residues encoding the peptide for the tumor-specific neoantigen and the flanking regions as well as the amino acid residue positions. A HLA allele pseudo-sequence that represents a HLA allele is obtained. The HLA pseudo-sequence can be at least about 20 to about 100 amino acids in length. Preferably, the HLA pseudo-sequence is at least about 30 to 60 amino acids in length. The HLA allele pseudo-sequence is encoded into a corresponding numerical vector. The HLA allele can be type A, B, or C, DQ, DP, or DR.

A neural network model is then used to jointly predict the tumor-specific neoantigen MHC class I or MHC class II binding affinity and for each peptide of interest a numerical probability that a corresponding peptide will be presented by a MHC class I or MHC class II protein on a cell-surface. The neural network model can be a pan-allele model, an allele-specific model, a super-type specific model, or combinations thereof.

Initially, the neural network model is trained on a training data set to optimize the performance of the neural network model. The training data set comprises peptide-MHC class I or MHC class II affinity measurement data sets and cell-surface peptide presentation data sets. Preferably, the neural network model is trained on positive training data as well as negative training data. The negative training data can comprise peptides that do not have tumor-specific neoantigen MHC class I or MHC class II binding affinity and/or are not presented by a MHC class I or MHC class II protein on a cell-surface.

The model input layer comprises the numerical vector comprising the peptide sequence for the tumor-specific neoantigen and the flanking regions and the numerical vector comprising the numerical vector comprising the HLA allele pseudo-sequence. Next, each of the numerical vectors are encoded into an amino acid embedding layer. The neural network model then flattens the amino acid embedding layer to produce a numerical vector representation for each peptide sequence of the tumor-specific neoantigen and the peptide sequence flanking regions, and the HLA allele pseudo-sequence.

To predict the peptide tumor-specific neoantigen MHC class I or MHC class II binding affinity, the tumor-specific neoantigen peptide sequence and the HLA allele pseudo-sequence are concatenated. The model further comprises applying one or more layers and/or one or more activation functions. For example, the model can comprises applying one or more connected layers. For example, the model can comprise applying a dropout layer. For example, the model can comprises applying a activation function. In instances, the model may comprise applying one or more connected layers, applying one or more dropout layers, and/or applying an activation function. The output is a numerical score representing the peptide ligand-MHC class I or MHC class II binding affinity. To predict the probability that the tumor-specific neoantigen will be presented by a MHC class I or MHC class II protein on a cell-surface, the peptide sequence of interest, the peptide sequence flanking regions, and the HLA allele pseudo-sequence are concatenated into a single numerical vector. The predicted peptide ligand-MHC class I or MHC class II binding affinity is also concatenated. The model further comprises applying one or more layers and/or one or more activation functions. For example, the model can comprise applying one or more connected layers. For example, the model can comprise applying a dropout layer. For example, the model can comprise applying an activation function. The model can further comprise applying one or more connected layers, applying a dropout layer, and/or applying an activation function. The output is a numerical probability that a peptide will be presented by a MHC class I or MHC class II protein on a cell-surface. The tumor-specific neoantigen MHC class I or MHC class II binding affinity and the numerical probability that the tumor-specific neoantigen will be presented by a MHC class I or MHC class II protein on a cell-surface is a proxy for tumor-specific neoantigen MHC class I immunogenicity. Generally, MHC class I immunogenicity is CD8+ T-cell immunogenicity. MHC class II immunogenicity is CD4+ immunogenicity.

The method can further comprise validating the neural network by applying one or more ranking metrics to an immunogenicity validation data set, ranking peptides for each allele in the immunogenicity validation data set based on the peptide's predicted MHC class I binding affinity and the numerical probability that a peptide will be presented by a MHC class I protein on a cell-surface, and aggregating the ranking metrics for all alleles. The ranking metrics can be aggregated by using weighted allele frequencies. The method can additionally comprise calibrating the neural network model. The neural network model can be calibrated with a probabilistic computation. The computation can estimate the overall presentation probability for a subject's alleles.

Tumor-specific neoantigens that are predicted to be MHC class I or MHC class II immunogenic can be selected for an immunogenic composition. Typically, about 10 to about 20 tumor-specific neoantigens can be selected for the immunogenic composition.

3. BRIEF DESCRIPTION OF DRAWINGS

FIG. 1 is a model architecture diagram. Model inputs: a) peptide sequence (plus flanking regions); b) allele pseudo-sequence. Model outputs: a) Predicted binding affinity; b) predicted presentation probability. Loss functions used for training the models: a) MSE-with-inequalities loss for binding affinity predictions; b) binary focal loss for predicting presentation probability.

FIG. 2A is a graph depicting the rate of peptides which have no partner peptide with similarity greater than the threshold. FIG. 2B is a graph showing the distribution of peptide length across three datasets (affinity, presentation, and immunogenicity).

FIG. 3 is a graph showing peptide-MHC binding affinity label distribution. The y-axis represents the rate of samples in the training data that belong to each bin.

FIG. 4 is a graph showing the distribution of HLA allele supertypes in the dataset samples.

FIGS. 5A-5C are graphs depicting sample distribution per HLA alleles. FIG. 5A shows the sample distribution for peptide MHC-binding affinity. FIG. 5B shows the sample distribution for cell-surface peptide presentation. FIG. 5C shows the sample distribution for T-cell immunogenicity.

FIG. 6 is a graph depicting immunogenicity allele frequency weights, based on allele frequency in the US population.

FIG. 7 is a graph showing a performance comparison with different values of alpha, which determines the weight of each loss component.

FIG. 8A and FIG. 8B are graphs showing the correlation between immunogenicity rate and predicted presentation probability (FIG. 8A) and predicted binding affinity (FIG. 8B). This experiment was performed over the immunogenicity validation set where the ground truth immunogenicity labels are known and predicted presentation and binding affinity using a pan model.

FIG. 9 illustrates an example provider network environment.

FIG. 10 is a block diagram of an example provider network that provides a storage service and a hardware virtualization to customers according to some embodiments.

FIG. 11 is a block diagram illustrating an example computer system.

FIG. 12 shows a model input. The model receives two sequences, a token sequence and a corresponding segment sequence. The token sequence is composed by concatenating the <CLS> token, allele pseudo-sequence tokens, <SE[> token, n-flank tokens, peptide, c-flank tokens and an <EOS> token. The segment sequence provides a corresponding index indicating to which segment the corresponding token belongs to. FIG. 12 discloses SEQ ID NO: 4.

FIG. 13 is a schematic of a transformer layer composed of a multi-head self-attention module followed by a feed-forward module (composed of 2 linear layers with GELU activation in between). Layer normalization is applied in the beginning of each module and residual dropouts are applied at the end of each components before residual connection.

4. DETAILED DESCRIPTION

The disclosure relates to novel methods for predicting tumor-specific neoantigen MHC class I or MHC class II immunogenicity by jointly predicting either MHC class I or MHC class II binding affinity and predicting the likelihood the tumor-specific neoantigen will be presented by a MHC class I or MHC class II protein on a cell-surface. The novel methods are preferably used to predict tumor-specific neoantigen MHC class I or MHC class II immunogenicity.

The methods include obtaining sequencing data for a tumor specific neoantigen and a HLA allele pseudo-sequence that represents a HLA allele. Exome, transcriptome and/or whole genome nucleotide sequencing, for example, can be used to obtain sequencing data and peptide sequence for a tumor-specific neoantigen. The methods may further include encoding the peptide sequence for each tumor-specific neoantigen and optionally the flanking regions into a corresponding numerical vector. Each numerical vector includes information describing the amino acids that comprise the peptide sequence and the positions of the amino acid sequence.

The methods may also comprise encoding the HLA pseudo-sequence into a numerical vector. The methods may include inputting the numerical vectors into a neural network model to jointly predict the tumor-specific neoantigen MHC class I or MHC class II binding affinity and a numerical probability for each tumor-specific neoantigen that a corresponding peptide will be presented by a MHC class I or MHC class II protein on a cell-surface. Both of these predictions can be used as a proxy for predicting MHC class I or MHC class II immunogenicity (e.g., CD8+ T-cell immunogenicity or CD4+ T-cell immunogenicity). After the numerical vectors are inputted into the neural network model, the numerical vectors can be converted into an amino acid embedding layer, which can then be flattened to produce a numerical vector representation for each peptide sequence for the tumor-specific neoantigen, optionally the peptide flanking regions, and the HLA allele pseudo-sequence.

Next, the neural network model can be used to predict the tumor-specific neoantigen MHC class I or MHC class II binding affinity and the probability that the tumor-specific neoantigen will be presented by a MHC class I or MHC class II protein on a cell-surface. These predictions can be performed by concatenating the tumor-specific neoantigen peptide sequence, the HLA allele pseudo-sequence, and optionally the peptide flanking regions. Then one or more layers and/or functions can be applied. For example, one or more fully-connected dense layers can be applied. For example, one or more dropout layers can be applied. For example, one or more activation functions can be applied. In embodiments, a combination of one or more fully-connected dense layers, one or more dropout layers, and/or one or more activation functions may be applied. The output is a numerical score representing the tumor-specific MHC class I or MHC class II binding affinity and/or a numerical probability that a peptide will be presented by a MHC class I or MHC class II protein on a cell-surface. These predictive values can be a proxy for immunogenicity. Immunogenic tumor-specific neoantigens can then be selected for inclusion in a personalized immunogenic composition.

The predictions disclosed herein are identified based on a training data set. The training data set comprises a plurality of samples. The training data set can comprise peptide MHC class I or MHC class II affinity measurement data sets and cell-surface peptide presentation data sets. Preferably, the neural network model is trained on positive training data, as well as negative training data. The negative training data can comprise peptides that do not have tumor-specific neoantigen MHC class I or MHC class II binding affinity and/or are not presented by a MHC class I or MHC class II protein on a cell-surface.

Neoantigens that are predicted to be MHC class I or MHC class II immunogenic can be selected for inclusion in an immunogenic composition. Typically, about 10 to about 20 tumor-specific neoantigens can be selected for the immunogenic composition. For example, about the immunogenic composition may comprise about 5, about 6, about 7, about 8, about 9, about 10, about 11, about 12, about 13, about 14, about 15, about 16, about 17, about 18, about 19, about 20, about 21, about 22, about 23, about 24, or about 25 tumor-specific neoantigens.

I. Definitions

All publications and patents cited in this disclosure are incorporated by reference in their entirety. To the extent, the material incorporated by reference contradicts or is inconsistent with this specification, the specification will supersede any such material. The citation of any references herein is not an admission that such references are prior art to the present disclosure. Various terms relating to aspects of the description are used throughout the specification and claims.

Such terms are to be given their ordinary meaning in the art unless otherwise indicated. Other specifically defined terms are to be construed in a manner consistent with the definitions provided herein.

As used herein, the singular forms "a," "an," and "the" include plural forms unless the context clearly indicates otherwise. The terms "include," "such as," and the like are intended to convey inclusion without limitation, unless otherwise specifically indicated.

As used herein, the term "cancer" refers to the physiological condition in subjects in which a population of cells is characterized by uncontrolled proliferation, immortality, metastatic potential, rapid growth and proliferation rate and/or certain morphological features. Often cancers can be in the form of a tumor or mass, but may exist alone within the subject, or may circulate in the blood stream as independent cells, such as leukemia or lymphoma cells. The term cancer includes all types of cancers and metastases, including hematological malignancy, solid tumors, sarcomas, carcinomas and other solid and non-solid tumors. Examples of cancers include, but are not limited to, carcinoma, lymphoma, blastoma, sarcoma, and leukemia. More particular examples of such cancers include squamous cell cancer, small cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer (e.g., triple negative breast cancer, hormone receptor positive breast cancer), osteosarcoma, melanoma, colon cancer, colorectal cancer, endometrial (e.g., serous) or uterine cancer, salivary gland carcinoma, kidney cancer, liver cancer, prostate cancer, vulvar cancer, thyroid cancer, hepatic carcinoma, and various types of head and neck cancers. Triple negative breast cancer refers to breast cancer that is negative for expression of the genes for estrogen receptor (ER), progesterone receptor (PR), and Her2/neu. Hormone receptor positive breast cancer refers to breast cancer that is positive for at least one of the following: ER or PR, and negative for Her2/neu (HER2).

The term "neoantigen" as used herein refers to an antigen that has at least one alteration that makes it distinct from the corresponding parent antigen, e.g., via mutation in a tumor cell or post-translational modification specific to a tumor cell. A mutation can include a frameshift, indel, missense or nonsense substitution, splice site alteration, genomic rearrangement or gene fusion, or any genomic expression alteration giving rise to a neoantigen. A mutation can include a splice mutation. Post-translational modifications specific to a tumor cell can include aberrant phosphorylation. Post-translational modifications specific to a tumor cell can also include a proteasome-generated spliced antigen. See, Lipe et al., Science, 354(6310):354:358 (2016). In general, point mutations account for about 95% mutations in tumors and indels and frame-shift mutations account for the rest. See, Snyder et al., N Engl J Med., 371:2189-2199 (2014).

As used herein the term "tumor-specific neoantigen" is a neoantigen present in a subject's tumor cell or tissue, but not in the subject's normal cell or tissue.

As used herein the term "immunogenic" as used herein refers to the ability to elicit an immune response (e.g., a T-cell response, a B-cell response, or both).

As used herein the term "HLA allele pseudo-sequence" refers to an amino acid sequence that is generated by a algorithm to represent a HLA allele amino acid sequence.

The term "subject" as used herein refers to any animal, such as any mammal, including but not limited to, humans, non-human primates, rodents, and the like. In some embodiments, the mammal is a mouse. In some embodiments, the mammal is a human.

The term "tumor cell" as used herein refers to any cell that is a cancer cell or is derived from a cancer cell. The term "tumor cell" can also refer to a cell that exhibits cancer-like properties, e.g., uncontrollable reproduction, resistance to anti-growth signals, ability to metastasize, and loss of ability to undergo programed cell death.

As used herein, the term "neural network" refers to a machine learning model for classification or regression consisting of multiple layers of linear transformations followed by element-wise nonlinearities typically trained via stochastic gradient descent and back-propagation.

Any terms not directly defined herein shall be understood to have the meaning commonly associated with them as understood within the art of the invention. Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

Additional description of the methods and guidance for the practice of the methods are provided herein. For ease of presentation, further details and guidance are provided with respect to a preferred aspect of predicting MHC class I immunogenicity by jointly predicting MHC class I binding affinity and predicting the likelihood that the tumor-specific neoantigen will be presented by a MHC class I protein on a cell-surface. It is intended that further details and guidance also relate to predicting MHC class II immunogenicity.

II. Training

The neural network model can include training the neural network model on a training data set to optimize the performance of the neural network model so that the neural network can predict tumor-specific neoantigen MHC class I or MHC class II binding affinity and the probability that the tumor-specific neoantigen will be presented by a MHC class I or MHC class II protein on a cell-surface.

The training data set used in the methods described herein contains a plurality of samples. The training data may include various data. The training data set can comprise a peptide MHC class I or MHC class II affinity measurement data set and a cell-surface peptide presentation data set, and optionally an immunogenicity data set. The training data set can comprise human rhinovirus data. Negative samples can be used for the immunogenicity evaluation. The training data set can be used to train one or more neural network models. In embodiments, one or more neural network models can be trained. For example, at least 2 or more neural networks may be trained. At least about 3, 4, 5, 6, 7, 8, 9, 10 or more neural networks can be trained.

The data set comprising peptide MHC class I or MHC class II affinity measurement data can comprise experimentally measured binding affinity peptides to a specific MHC class I allele or MHC class II allele. The data set can be obtained from one or more data sources, such as publicly available data sources. For example, the data set may be obtained from the Immune Epitope Database ("IEDB," iedb.org). The training data set can be further augmented based on one or more data sources. The training data set can be further curated for the methods disclosed herein. For example, the training data may contain binding affinity predictions between a peptide and each of the associated MHC molecules. The experimentally measured binding affinities in the data set can be quantitative (associated with an inequality of "="), qualitative (associated with an inequalities of "<" or ">"), or a combination thereof. The quantitative data can comprise IC50 mM values. Qualitative data sets can be represented as positive-high (e.g., a binding affinity of <100 nm), positive-intermediate (e.g., a binding affinity of <1,000 nm), positive low (e.g., a binding affinity of <5,000 nm), or negative (e.g., a binding affinity of >5,000 nm). The training data set comprising MHC class I or MHC class II affinity measurement data sets can comprise peptides eluted from MHC and identified by mass spectrometry.

MHC class I affinity measurement data set can be further curated to retain a subset of predicted binding affinities for a specific MHC class I peptide allele. For example, entries for HLA-A, HLA-B, and/or HLA-C alleles can be retained. For example, peptides of a particular length can be retained. Peptides that are at least about 5 amino acids in length to about 20 amino acids in length can be retained. The peptides may have an amino acid length of about 5, 6, 7, 8, 9, 10, 11, 12, 13, 14, 15, 16, 17, 18, 19, or 20 amino acids. The peptides in the training set can be the same or different lengths and may vary depending on the type of MHC allele. Preferably, the peptides have a length of about 5 to about 15 amino acids. Peptides containing post-translational modifications or noncanonical amino acids can be dropped.

MHC class II affinity measurement data set can be further curated to retain a subset of predicted binding affinities for a specific MHC class II peptide allele. For example, entries for HLA-DP, HLA-DQ, and/or HLA-DR alleles can be retained. For example, peptides of a particular length can be retained. Peptides that are at least about 5 amino acids in length to about 40 amino acids in length can be retained. The peptides may have an amino acid length of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids. The peptides in the training set can be the same or different lengths and may vary depending on the type of MHC allele. Typically, the peptides have a length of about 13 to about 35 amino acids. Peptides containing post-translational modifications or noncanonical amino acids can be dropped.

The MHC class I or MHC class II affinity measurement data can be provided as a regression model. In particular a loss function can be used. Exemplary loss functions include, cross-entropy loss function, the mean square error, the huber loss, Kullback-Leibler, MAE (L1), MAE (L3), likelihood function, and the hinge loss. In particular, a variation of mean square loss function can be used. Mean square loss function can be denoted by $L_{BA-MSE}$, in which measurements are associated with (>) or (<), contribute to the loss only when inequality is violated, for handling both quantitative and qualitative peptide-MHC binding affinity measurements in the dataset. The expression that can be employed is:

$$L_{BA\text{-}MSE} = \frac{1}{N}\sum_{i=1}^{N} l(\acute{Y}_i, Y_i)$$

$$l(\acute{Y}_i, Y_i) = \begin{cases} (Y_i - \acute{Y}_i)^2, & \text{if inequality for measurement } i \text{ is } (=) \\ \max(\acute{Y}_i - Y_i, 0)^2, & \text{if inequality for measurement } i \text{ is } (<) \\ \max(Y_i - \acute{Y}_i, 0)^2, & \text{if inequality for measurement } i \text{ is } (>) \end{cases}$$

Scheme 1

Yi and Ýi represent the target and predicted peptide-MHC binding affinity values for the i-th sample. The affinity targets can be converted before training. The IC50 nM values in [0, 50000] range to target values within the [0,1] range. The following function can be employed to convert the IC50 nM values:

$$Y_i = 1 - \frac{\log IC50_i}{\log 50000}$$

Scheme 2

The MHC class I or MHC class II affinity measurement data set can comprise at least about 5,000, about 10,000, about 15,000, about 20,000, about 25,000, about 30,000, about 35,000, about 40,000, about 45,000, about 50,000, about 60,000, about 70,000, about 80,000, about 90,000, about 100,000, about 150,000, about 200,000, about 250,000, about 300,000, about 350,000, about 400,000, about 450,000, about 500,000, about 550,000, about 600,000, about 650,000, about 700,000, about 750,000, about 800,000, about 850,000, about 900,000, about 950,000, about 1,000,000, about 1,250,000, about 1,500,000, about 1,750,000, about 2,000,000 or more measurements of binding affinity of peptides to MHC class I or MHC class II peptide alleles. Generally, the MHC class I or MHC class II affinity measurement data set comprises at least about 20,000 unique peptides.

The cell-surface peptide presentation data set can comprise peptides that are known to be presented via HLA molecules. The cell-surface peptides can be determined by peptide elution experiments or by mass spectrometry data, for example. The cell-surface peptide presentation data set can be obtained from one or more data sources, such as publicly available data sources. For example, the Immune Epitope Database ("IEDB," iedb.org) or peptides generated in the SysteMHC project may be a useful data source. The cell-surface peptide presentation data set can further be experimentally produced. For example, peptides can be prepared by diluting peptides from cell lines that express HLA peptides and analyzing the peptides by mass spectrometry. The training data sets can be further augmented based on one or more data sources.

These training data sets are typically curated for the methods disclosed herein. The peptide sequences are generally represented as character strings, wherein each character represents an amino acid. The peptide sequences can be converted into a numerical vector that includes information describing the amino acids of the peptide and the positions of the amino acid. The numerical vector may be a binary classification. For example, a peptide sequence, p', with k' amino acids is represented by a row vector of 20 amino acids (20-k), where a single element that corresponds to the alphabet of the amino acid at a particular position of the peptide sequence will have a value of 1. The remaining elements will have a value of 0. As an example, for an amino acid alphabet of A, C, D, E, F, G, H, I, K, L, M, N, P, Q, R, S, T, V, W, and Y, the peptide sequence AFP of 3 amino acids may be represented by a row vector of 60 elements and $p^i=1$ 0 0 0 0 0 0 0 0 0 0 0 0 0 0 0 0 0 0 0 0 1 0 0 0 0 0 0 0 0 0 0 0 0 0 0 0 0 0 0 0 0 0 0 0 0 0 0 0 0 1 0 0 0 0 0 0 0. When the training data set comprises amino acid sequences of varying lengths, the numerical vector can comprise padding characters to encode the peptides into equal lengths. The padding characters can be applied left of the peptide sequence or right of the peptide sequence. One of skill in the art will recognize that other types of classification systems may be applied.

A loss function can be employed to the cell-surface peptide presentation data set. Exemplary loss functions include, cross-entropy loss function, the mean square error, the huber loss, Kullback-Leibler, MAE (L1), MAE (L3), likelihood function, and the hinge loss. In particular, a cross-entropy loss function can be employed by the cell-surface peptide presentation data set. In a particular embodiment, focal loss binary classification can be used. A focal loss binary classification can be employed to reduce imbalance in the dataset. Focal loss can be denoted as LP-FL, which is a weighted extension of the standard binary cross-entropy loss that gives more emphasis to poorly classified samples. The focal loss expression is as follows:

$$L_{P\text{-}FL} = \frac{1}{N}\sum_{i=1}^{N}(1 - p_{t_i})^\gamma \log p_{t_i},$$

where the predicted probability of the correct class $p_{t_i}$ is $$p_{t_i} = \begin{cases} \hat{Y}_i, & Y_i = 1 \\ 1 - \hat{Y}_i, & Y_i = 0 \end{cases}$$

Scheme 3

$\gamma$ is a real parameter, which is set to 1. In the binary case $Y_i \varepsilon \{0, 1\}$ is the ground truth label and $\hat{Y}_i$ is the predicted presentation probability for the i-th sample.

A ranking objective can further be employed to the cell-surface peptide presentation data set for training. For example, N-way classification can be used for the ranking orientated training. The N-way classification allows the positive samples to compete with the negative samples in the data set. The samples can then be classified for which each set of N samples are positive samples (N=number of negative-samples +1). For N-way classification loss, cross-entropy or focal loss function can be applied.

The cell-surface peptide presentation data set can comprise at least about 5,000, about 10,000, about 15,000, about 20,000, about 25,000, about 30,000, about 35,000, about 40,000, about 45,000, about 50,000, about 60,000, about 70,000, about 80,000, about 90,000, about 100,000, about 150,000, about 200,000, about 250,000, about 300,000, about 350,000, about 400,000, about 450,000, about 500, 000, about 550,000, about 600,000, about 650,000, about 700,000, about 750,000, about 800,000, about 850,000, about 900,000, about 950,000, about 1,000,000, about 1,250,000, about 1,500,000, about 1,750,000, about 2,000, 000 or more peptides. Training data sets larger than 35,000 samples are preferable.

The neural network model can be trained on all of the training data or a portion thereof. For example, the neural network model can be trained on about 100% of the training data, about 95%, about 90%, about 85%, about 80%, about 75%, about 70%, about 65%, about 60%, about 55% or less of the training data set. The neural network model can be trained on all training data in the MHC class I or MHC class II affinity measurement set and all training data in the cell-surface peptide presentation training data set. For example, the neural network model can be trained on about 100%, about 95%, about 90%, about 85%, about 80%, about 75%, about 70%, about 65%, about 60%, about 55% or less of the MHC class I or MHC class II affinity measurement data set and/or about 100%, about 95%, about 90%, about 85%, about 80%, about 75%, about 70%, about 65%, about 60%, about 55% or less of the cell-surface peptide presentation training data set.

In one implementation, training data from one or more training data sets can be cross-trained. For instance, the MHC class I or MHC class II affinity measurement data set and the cell-surface peptide presentation data set can be cross-trained. Each data set typically comprises a single known target. For example, the MHC class I or MHC class II affinity measurement data comprises peptide affinities and the cell-surface peptide presentation data set comprise peptides that can be presented by MHC class I or MHC class II proteins on a cell-surface. To cross-train the training data sets, targets for each trained set can be inferred. For instance, peptides that present on the cell-surface can be inferred to have high binding affinity values and peptides that are not presented on the cell-surface can be inferred to have a low binding affinity. For instance, peptides with a high binding affinity can be inferred to present peptides on the cell-surface and peptides with a low binding affinity can be inferred to not present peptides on the cell-surface.

In one implementation, self-distillation can be performed on the training data from one or more training data sets. Self-distillation can be performed by extracting binding affinity and presentation estimates for a plurality of samples. These samples can be added to corresponding weak labels to the training dataset. Self-distillation can be carried out using multi-allelic spectrometry data. Self-distillation can be carried out using positive presenters. For positive presenters in the training data set with unknown binding affinity, the binding affinity can be estimated using an established model.

The neural network model is preferably trained on positive training data and negative training data to limit biases. Training a network on an imbalanced dataset can make the neural network model biased by learning more representations of the data dominated class and other classes can be overlooked. For instance, a neural network model trained only on a positive training data set may be biased towards overpredicting the peptide tumor-specific neoantigen MHC class I or MHC class II binding affinity or overpredicting the probability that the tumor-specific neoantigen will be presented by a MHC class I or MHC class II protein on a cell-surface. A neural network model trained only on a negative training set may be biased towards underestimating the peptide tumor-specific neoantigen MHC class I or MHC class II binding affinity or underestimating the likelihood that the tumor-specific neoantigen will be presented by a MHC class I or MHC class II protein on a cell-surface.

The MHC class I or MHC class II affinity measurement data set typically comprises both positive training data and negative training data. For example, positive training data can include binding affinity predictions that are classified as positive (e.g., a binding affinity of <5,000 nm). For example, negative training data can include binding affinity predictions that are negative (e.g., a binding affinity of >5,000 nm). If desired, additional negative training data can be incorporated into the training set by augmenting the training data set to include random peptides with low affinity. For example, the random peptides may have a qualitative weak affinity target of about >20,000 nm.

The cell-surface peptide presentation training data set typically comprises positive training data (e.g., peptides that are presented by a MHC class I protein on a cell-surface) and do not contain negative training data (e.g., peptides that cannot be presented by a MHC class I protein on a cell-surface). When the training data set does not contain negative training data, the positive training data set can be used to generate a probabilistic negative training data set (e.g., a negative training data set derived from the positive training data set). A negative training data set can be generated by shuffling the 'positive' peptides for a HLA allele. The peptides can be shuffled by changing the amino acid length (e.g., making the peptide longer or shorter). Alternatively, the peptide amino acid sequence can be modified by, for example, amino acid substitutions, insertions, or deletions. Insertions include amino and/or carboxyl terminal fusions as well as intrasequence insertions or multiple amino acid residues. Deletions are characterized by the removal of one or more amino acid residues from the peptide sequence. Amino acid substitutions are typically single residue substitutions, but can occur at multiple locations. Substitutions, deletions, insertions or any combination thereof may be combined to arrive at a peptide that is not presented by a MHC class I or MHC class II protein on a cell-surface. For example, a peptide sequence having the amino acid sequence of: AVGGGERRYIKL (SEQ ID NO: 1) can be modified to: CVGGGEHRYIMNNL (SEQ ID NO: 2).

In addition, or in combination with the peptide shuffling, HLA shuffling can be used to generate a negative training data set. HLA alleles classified as 'positive' (e.g., a HLA allele that presents a corresponding peptide on the cell-surface), can be replaced with a different allele which does not belong to the positive allele supertype.

In addition, or in combination with the peptide shuffling and/or HLA shuffling, HRV negative sampling can be used to generate a negative training data set.

The training data can further be filtered to remove redundant peptides. For example, peptides that are duplicates (e.g., are the same amino acid sequence) can be removed so that the training data set contains unique peptides. Those of skill in the art will readily understand how to determine the identity of peptides (i.e., determine if the peptides are the same or different).

The trained neural network model can be validated using an immunogenicity data set. Validating the neural network model can comprise applying one or more ranking metrics to an immunogenicity data set. The peptides in the immunogenicity validation data set can be ranked based on the peptide's predicted MHC class I or MHC class II binding affinity and the numerical probability that a peptide will be presented by a MHC class I or MHC class II protein on a cell-surface. The ranking metrics can be aggregated for all alleles. The ranking metrics can be aggregated by using weighted allele frequencies.

In implementations, the neural network model can be trained using unlabeled an unlabeled data set. For instance, peptides in the cell-surface peptide presentation data set may be unlabeled. Without being bound by theory, it is thought that unlabeled data sets (e.g., peptide sequences) may provide a numerical vector representation that can more accurately characterize inputted peptide sequences.

III. Model Architecture

The disclosure relates to using a neural network model to jointly predict tumor-specific neoantigen MHC class I or MHC class II binding affinity and a numerical probability for each peptide of interest that a corresponding peptide will be presented by a MHC class I or MHC class II protein on a cell-surface (i.e., the surface of a tumor cell). The neural network model is suitable for tumor-specific neoantigens that the neural network model has or has not previously encountered in training.

The neural network model may be a single neural network that includes a series of nodes arranged in one or more layers. The nodes may be connected to other nodes through connections each having an associated parameter. A value at one particular node may be represented as a sum of the values of nodes connected to the particular node weighted by the associated parameter mapped by an activation function associated with the particular node. The neural network model used in the methods described herein can be a pan-allele model, an allele-specific model, a super-type specific model, or a combination thereof.

In one particular implementation, the methods comprise converting a peptide sequence for a tumor-specific neoantigen into a numerical vector. The peptide sequence is usually represented as character strings where each character represents an amino acid. The peptide sequences can be converted into a numerical vector that include information describing the amino acids of the peptide and the positions of the amino acid. The numerical vector may be a binary classification. For example, a peptide sequence, $p^i$, with $k^i$ amino acids is represented by a row vector of 20 amino acids (20-k), where a single element that corresponds to the alphabet of the amino acid at a particular position of the peptide sequence will have a value of 1. The remaining elements will have a value of 0. As an example, for an amino acid alphabet of A, C, D, E, F, G, H, I, K, L, M, N, P, Q, R, S, T, V, W, and Y, the peptide sequence AGQY of 4 amino acids (SEQ ID NO: 3) may be represented by a row vector of 80 elements and $p^i$=1 0 0 0 0 1 0 0 0 0 0 0 0 1 0 0 0 0 0 1 1 0 0 0 0 1 0 0 0 0 0 0 0 1 0 0 0 0 0 1 1 0 0 0 0 1 0 0 0 0 0 0 1 1 0 0 0 0 1 0 0 0 0 0 0 1 0 0 0 0 0 1 .

The peptide sequences for a tumor-specific neoantigen can be about 5 amino acids in length to about 40 amino acids. For example, the peptide sequence can be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids. MHC class I molecules bind to short peptides. MHC class I molecules can accommodate peptides generally about 5 amino acids to about 10 amino acids in length. In embodiments, peptide sequences for a tumor-specific neoantigen are short peptides about 5 amino acids to about 10 amino acids in length. MHC class II molecules bind to peptides that are longer in length. MHC class II can accommodate peptides which are generally about 13 amino acids in length to about 25 amino acids in length. In embodiments, peptide sequences for a tumor-specific neoantigens are long peptides about 13 to 25 amino acids in length.

The peptide sequences for a tumor-specific neoantigen can be the same or different lengths. When the peptide sequences for a tumor-specific neoantigen are of differing lengths (e.g., one peptide sequence is 7 amino acids and one peptide sequence is 15 amino acids), a padding character can be added to the numerical vector such that each peptide for a tumor-specific neoantigen until the peptide reaches the maximum peptide length including the flanking region (e.g., 15 amino acids). A padding character can be added to the C-terminal or N-terminal of the flanking region. As an example, the padding characters would encode an amino acid of A, C, D, E, F, G, H, I, K, L, M, N, P, Q, R, S, T, V, W, and Y.

The peptide sequence for the tumor-specific neoantigen can comprise a sequence flanking the tumor-specific neoantigen peptide. The flanking sequence can be directly to the left of the tumor-specific neoantigen peptide sequence, directly to the right of the tumor-specific neoantigen peptide sequence, or both.

In embodiments, the peptide sequence for the tumor-specific neoantigen can comprise at least one of the C-terminal sequences flanking the tumor-specific neoantigen peptide within its source protein sequence or at least one N-terminal sequence flanking the tumor-specific neoantigen peptide within its source protein sequence. It is preferable that the peptide sequence for the tumor-specific neoantigen comprises at least one C-terminal amino acid sequence flanking the tumor-specific neoantigen peptide and at least one amino acid N-terminal sequence flanking the tumor-specific neoantigen peptide.

The flanking region can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more amino acids in length. The flanking region directly to the left of the tumor-specific neoantigen peptide can be 1, 2, 3, 4, 5, 6, 7, 8, 9, 10, 11, 12, 13, 14, 15, 16, 17, 18, 19, 20 or more amino acids in length. The flanking region directly to the right of the tumor-specific neoantigen peptide can be 1, 2, 3, 4, 5, 6, 7, 8, 9, 10, 11, 12, 13, 14, 15, 16, 17, 18, 19, 20 or more amino acids in length. In embodiments, the peptide sequence for the tumor-specific neoantigen comprises the flanking region directly left of the tumor-specific neoantigen can be up to about 10 amino acids in length and/or the flanking region directly right of the tumor-specific neoantigen can be up to about 10 amino acids in length. Preferably, the flanking region comprises a flanking region directly left of the tumor-specific neoantigen of 5 amino acids in length and a flanking region directly right of the tumor-specific neoantigen of 5 amino acids in length. The flanking region can similarly be encoded into the numerical vector as described above.

The methods further comprise converting a HLA allele pseudo-sequence into a numerical vector. The HLA allele pseudo-sequence represents a HLA allele. The HLA allele pseudo-sequence can be from about 5 amino acids to about 100 amino acids. For example, the HLA allele pseudo-sequence can be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids. The HLA allele pseudo-sequence may be about 30 to about 60 amino acids in length. In particular embodiments of the methods disclosed herein, the HLA allele pseudo-sequence is about 40 to about 50 amino acids in length.

The input of the neural network model can comprise (i) a numerical vector comprising a peptide sequence for a tumor-specific neoantigen and the flanking regions of the peptide sequence, and (ii) a numerical vector comprising the HLA allele pseudo-sequence. The input of the neural network can optionally comprise a segment identifier sequence. A segment identifier sequence informs the model to which segment each amino-acid belong. Next, the numerical vector comprising a peptide sequence for a tumor-specific neoantigen and the flanking regions of the peptide sequence, and (ii) a numerical vector comprising the HLA allele pseudo-sequence are encoded into one or more embedding layers. The embedding layer translates the high-dimensional vectors comprising a peptide sequence for a tumor-specific neoantigen and the flanking regions of the peptide sequence and numerical vector comprising the HLA allele pseudo-sequence into a low-dimensional space. The embedding layer can be considered the first layer of the neural network model. The embedding layer can then be flattened to produce a numerical vector representation for each peptide sequence for the tumor-specific neoantigen, the peptide flanking regions, and HLA allele pseudo-sequence.

To predict the peptide tumor-specific neoantigen MHC class I or MHC class II binding affinity, the tumor-specific peptide sequence and the HLA allele pseudo-sequence are concatenated. This means that the tumor-specific neoantigen peptide sequence and the HLA allele pseudo-sequence are linked together in a chain or a series. To predict the MHC class, I or MHC class II binding affinity, the flanking regions do not need to be concatenated. Although not necessary, in some instances it may be desirable to concatenate the flanking regions. Once the tumor-specific neoantigen peptide sequence and the HLA pseudo-sequence have been concatenated, one or more parameters (e.g., layers and/or functions) can be applied.

Exemplary layers that can be applied, include but are not limited to, fully connected dense layers, sequence layers, activation layers, normalization layers, dropout layers, cropping layers, pooling and unspooling layers, combination layers, object detection layers, or generation adversarial network layers.

Example fully connected dense layers include 2-D convolutional layer, 3-D convolutional layer, 2D grouped convolutional layers, transposed 2D-convolutional layer, transposed 3-D convolutional layer, or fully connected dense layers. Example sequence layers include, a sequence input layer, a LSTM layer, a bidirectional LSTM layer, a GRU layer, a sequence folding layer, a sequence unfolding layer, a flatten layer, or a word embedding layer. Example activation layers include a ReLU layer, a leaky ReLU layer, a clipped ReLU layer, a ELU activation layer, a hyperbolic tangent activation layer, or a PRELU layer. Example normalization, dropout, and cropping layers include a batch normalization layer, a group normalization layer, a channel-wise local response normalization layer, a dropout layer, a 2-D crop layer, a 3-D crop layer, a 2-D re-size layer, a 3-D re-size layer. Example pooling and unpooling layers include average pooling layer, a 3D layer, a global average pooling layer, a 3-D global average pooling layer, a maximum pooling layer, a 3-D maximum pooling layer, a global max pooling layer or a max unpooling layer. Example combination layers include an addition layer, a multiplication layer, a depth concatenation layer, a weighted average layer. Example object detection layers include ROI input layers, ROI max pooling layers, ROI align layer, am anchor box layer, a region proposal layer, a SSD merge layer, a space to depth layer, a regional proposal network, a focal loss layer, a region proposal network, a box regression.

In embodiments, one or more fully connected dense layers can be applied. A fully connected layer multiplies the input by a weight matrix and then adds a bias vector. For example, 1, 2, 3, 4, 5, 6, 7, 8, 9, 10, 11, 12, 13, 14, 15, 16, 17, 18, 19, 20 or more fully connected dense layers can be applied. It is preferable that at least 3 fully connected dense layers are applied when predicting MHC class I or MHC class II binding affinity.

In embodiments, one or more activation layers (functions) can be applied. The activation function can be assigned to a neuron or to an entire layer of the neuron. An exemplary activation function that can be applied is an ELU activation function or a reLU layer. Other activation layers described above and/or known to those skilled in the art can be applied. The activation function can transform the summed weighted input from a node into the activation of the node or output. For example, 1, 2, 3, 4, 5, 6, 7, 8, 9, 10, 11, 12, 13, 14, 15, 16, 17, 18, 19, 20 or more activation layers (functions) can be applied. Typically, about 1, 2, 3, 4, or 5 activation functions can be applied.

One or more dropout layers can be applied. A dropout layer is advantageous for reducing overfitting and thereby provides better results. For example, 1, 2, 3, 4, 5, 6, 7, 8, 9, 10, 11, 12, 13, 14, 15, 16, 17, 18, 19, 20 or more dropout layers can be applied. Typically, about 1, 2, 3, 4, or 5 dropout layers can be applied.

In an exemplary neural network model, one or more fully connected dense layers, one or more activation functions, and one or more dropout layers can be applied. In a preferred neural network model, one or more fully connected dense layers, a activation function (e.g., an ELU activation function), and one or a more dropout layers can be applied.

To enable better learning of sequence representations, one or more LSTM layers or one or more bi-directional-LTSM layers can be applied. A transformer may also be added. For example, about 1, about 2, about 3, about 4, about 5, about 6, about 7, about 8, about 9, about 10, about 11, about 12, about 13, about 14, about 15 or more transformer layers can be added. A transformer can add positional embedding into the embedded amino acid sequence and can comprise one or more stacked encoder layers. For example, the transformer can include one or more multi-head attention layers, one or more dropout layers, one or more normalization layers, one or more feed-forward layers or a combination thereof. An exemplary transformer can include: (1) a multi-head attention layer, (2) a dropout layer (0.1 rate), (3) a normalization layer, (4) a feed-forward later (linear layer and a ReLU layer), (5) a dropout layer (0.1 rate), and (6) a layer normalization).

A regression model can be applied to predict the peptide tumor-specific neoantigen MHC class I or Class II binding affinity. In particular, a variation of mean square loss function can be used. Mean square loss function can be denoted by $L_{BA\text{-}MSE}$, in which measurements are associated with (>) or (<), contribute to the loss only when inequality is violated, for handling both quantitative and qualitative peptide-MHC binding affinity measurements in the dataset. The expression that can be employed is shown in Schemes 1 and 2.

The output comprises a numerical score representing the peptide ligand-MHC class I or MHC class II binding affinity.

The neural network model further comprises jointly predicting the probability that the tumor-specific neoantigen will be presented by a MHC class I or MHC class II protein on a cell-surface. To predict the probability that the tumor-specific neoantigen will be presented by a MHC class I protein on a cell-surface, the tumor-specific peptide sequence, the corresponding flanking region, and the HLA allele pseudo-sequence are concatenated into a single numerical score.

Once the tumor-specific neoantigen peptide sequence, the corresponding flanking region and the HLA pseudo-sequence have been concatenated, one or more parameters (e.g., layers and/or functions) can be applied.

One or more fully connected dense layers can be applied. For example, 1, 2, 3, 4, 5, 6, 7, 8, 9, 10, 11, 12, 13, 14, 15, 16, 17, 18, 19, 20 or more fully connected dense layers can be applied. For predicting the probability that the tumor-specific neoantigen will be presented by a MHC class I or a class II protein on a cell-surface, it is preferable that at least 3 fully connected dense layers are applied.

One or more activation functions can be assigned to a neuron or to an entire layer of the neuron. An exemplary activation function that can be applied is an ELU activation function or a reLU layer. Other activation layers described above and/or known to those skilled in the art can be applied. The activation function can transform the summed weighted input from a node into the activation of the node or output. For example, 1, 2, 3, 4, 5, 6, 7, 8, 9, 10, 11, 12, 13, 14, 15, 16, 17, 18, 19, 20 or more activation layers (functions) can be applied. Typically, about 1, 2, 3, 4, or 5 activation functions can be applied.

One or more dropout layers can be applied. A dropout layer is advantageous for reducing overfitting and thereby provides better results. For example, 1, 2, 3, 4, 5, 6, 7, 8, 9, 10, 11, 12, 13, 14, 15, 16, 17, 18, 19, 20 or more dropout layers can be applied. Typically, about 1, 2, 3, 4, or 5 dropout layers can be applied.

A focal loss binary classification (See Scheme 3 above) can be employed to predict the probability that the tumor-specific neoantigen will be presented by a MHC class I or MHC class II protein on a cell-surface. The output is a numerical probability that a peptide will be presented by a MHC class I or MHC class II protein on a cell-surface.

The neural network model can further be calibrated. Neural networks can overestimate or underestimate probabilities if model is not calibrated. Thus, calibrating the neural network described herein can improve the accuracy and confidence of the predicted probabilities. To calibrate the neural network, a probabilistic computation can be applied. In particular, a probabilistic computation can be applied to one or more of the subject's HLA alleles. For example, 1, 2, 3, 4, 5, or 6 HLA alleles. The probabilistic computation can be used to estimate the overall presentation probability for the subject's alleles based on the model's prediction on each HLA allele. The neural network can further be calibrated by calibrating the neural networks presentation predictions on the validation data set. For example, a low degree polynomial to the calibration curve can be applied. Polynomial coefficients can be constrained to be positive to obtain a monotonic increasing function. Lasso linear regression can be used. The calibrated presentation predictions (e.g., the tumor-specific neoantigen MHC class I binding affinity and the probability that the tumor-specific neoantigen will be presented by a MHC class I protein on a cell-surface) can be used as a proxy for immunogenicity.

Performance of the neural network model can be evaluated using the immunogenicity data described herein. The neural network predictions can be evaluated by using one or more ranking metrics. Exemplary ranking metrics include, but are not limited to, top-k ranked items, Precision@K, $n$DCG$_K$, Reciprocal Rank, and Positive Predictive Value metric. All corresponding peptides for each allele in the immunogenicity data set can be ranked based on the predicted cell-surface peptide presentation probability and/or the predicted binding affinities scores using one or more ranking metrics. The ranking metrics can then be aggregated using weighted allele frequencies.

In one implementation, self-supervised pre-training can be performed. Exemplary training models are masked-language-modeling and next peptide prediction.

IV. Computer Implementation of Methods

A computer system programed or otherwise configured can be used to implement the methods disclosed herein. The computer system can include a single computing device or multiple computing devices that are interconnected using one or more computing networks. The computer system can execute the neural network model described herein using the computer capacity.

The computer system can include a central processing unit, which can be a single core or multi core processor, or plurality of processors for parallel processing. The system can include memory (e.g., random-access memory, rad-only memory, flash memory), electronic storage unit (e.g., a could platform), communications interface for communicating with one or more systems, and other peripheral devices such as data storage, other memory, and display adaptors. The memory, storage device, interface, and peripheral devices can be in communication with the CPU through a communications bus. Any one or all of these components can communicate via a shared internal network or an external network, and the collective system can communicate with one or more of the user devices via the network. The network can be the internet, an extranet, or an internet/extranet that is in communication with the internet. The network can include one or more computer servers, which can enable distributed computing, such as cloud computing. The computer system can be in communication with a processing system. The processing system can be configured to implement the methods disclosed herein.

Various examples of the computing device can include, but are not limited to, a desktop computer, laptop, and a mobile phone, tablet computer, personal computer, wearable computer, server, personal digital assistant (PDA), hybrid PDA/mobile phone, mobile phone, electronic book reader, set-top box, voice command device, camera, digital media player, and the like. In some embodiments, the computer device can have one or more user interfaces, command-line interfaces (CLI), application programing interfaces (API), and/or other programmatic interfaces for submitting training requests, deployment requests, and/or execution requests. In some embodiments, the computer device can execute a stand-alone application that interacts with the neural network model.

In some embodiments, the network includes any wired network, wireless network, or combination thereof. For example, the network may be a personal area network, local area network, wide area network, over-the-air broadcast network (e.g., for radio or television), cable network, satellite network, cellular telephone network, or combination thereof. As a further example, the network may be a publicly accessible network of linked networks, possibly operated by various distinct parties, such as the Internet. In some embodiments, the network may be a private or semi-private network, such as a corporate or university intranet. The network may include one or more wireless networks, such as a Global System for Mobile Communications (GSM) network, a Code Division Multiple Access (CDMA) network, a Long Term Evolution (LTE) network, or any other type of wireless network. The network can use protocols and components for communicating via the Internet or any of the other aforementioned types of networks. For example, the protocols used by the network may include HTTP, HTTP Secure (HTTPS), Message Queue Telemetry Transport (MQTT), Constrained Application Protocol (CoAP), and the like. Protocols and components for communicating via the Internet or any of the other aforementioned types of communication networks are well known to those skilled in the art and, thus, are not described in more detail herein.

FIG. 9 illustrates an example provider network (or "service provider system") environment according to some embodiments. A provider network 900 may provide resource virtualization to customers via one or more virtualization services 910 that allow customers to purchase, rent, or otherwise obtain instances 912 of virtualized resources, including but not limited to computation and storage resources, implemented on devices within the provider network or networks in one or more data centers. Local Internet Protocol (IP) addresses 916 may be associated with the resource instances 912; the local IP addresses are the internal network addresses of the resource instances 912 on the provider network 900. In some embodiments, the provider network 900 may also provide public IP addresses 914 and/or public IP address ranges (e.g., Internet Protocol version 4 (IPv4) or Internet Protocol version 6 (IPv6) addresses) that customers may obtain from the provider 900.

Conventionally, the provider network 900, via the virtualization services 910, may allow a customer of the service provider (e.g., a customer that operates one or more client networks 950A-950C including one or more customer device(s) 952) to dynamically associate at least some public IP addresses 914 assigned or allocated to the customer with particular resource instances 912 assigned to the customer. The provider network 900 may also allow the customer to remap a public IP address 914, previously mapped to one virtualized computing resource instance 912 allocated to the customer, to another virtualized computing resource instance 912 that is also allocated to the customer. Using the virtualized computing resource instances 912 and public IP addresses 914 provided by the service provider, a customer of the service provider such as the operator of customer network(s) 950A-950C may, for example, implement customer-specific applications and present the customer's applications on an intermediate network 940, such as the Internet. Other network entities 920 on the intermediate network 940 may then generate traffic to a destination public IP address 914 published by the customer network(s) 950A-950C; the traffic is routed to the service provider data center, and at the data center is routed, via a network substrate, to the local IP address 916 of the virtualized computing resource instance 912 currently mapped to the destination public IP address 914. Similarly, response traffic from the virtualized computing resource instance 912 may be routed via the network substrate back onto the intermediate network 940 to the source entity 920.

Local IP addresses, as used herein, refer to the internal or "private" network addresses, for example, of resource instances in a provider network. Local IP addresses can be within address blocks reserved by Internet Engineering Task Force (IETF) Request for Comments (RFC) 1918 and/or of an address format specified by IETF RFC 4193 and may be mutable within the provider network. Network traffic originating outside the provider network is not directly routed to local IP addresses; instead, the traffic uses public IP addresses that are mapped to the local IP addresses of the resource instances. The provider network may include networking devices or appliances that provide network address translation (NAT) or similar functionality to perform the mapping from public IP addresses to local IP addresses and vice versa.

Public IP addresses are Internet mutable network addresses that are assigned to resource instances, either by the service provider or by the customer. Traffic routed to a public IP address is translated, for example via a 1:1 NAT, and forwarded to the respective local IP address of a resource instance.

Some public IP addresses may be assigned by the provider network infrastructure to particular resource instances; these public IP addresses may be referred to as standard public IP addresses, or simply standard IP addresses. In some embodiments, the mapping of a standard IP address to a local IP address of a resource instance is the default launch configuration for all resource instance types.

At least some public IP addresses may be allocated to or obtained by customers of the provider network 900; a customer may then assign their allocated public IP addresses to particular resource instances allocated to the customer. These public IP addresses may be referred to as customer public IP addresses, or simply customer IP addresses. Instead of being assigned by the provider network 900 to resource instances as in the case of standard IP addresses, customer IP addresses may be assigned to resource instances by the customers, for example via an API provided by the service provider. Unlike standard IP addresses, customer IP addresses are allocated to customer accounts and can be remapped to other resource instances by the respective customers as necessary or desired. A customer IP address is associated with a customer's account, not a particular resource instance, and the customer controls that IP address until the customer chooses to release it. Unlike conventional static IP addresses, customer IP addresses allow the customer to mask resource instance or availability zone failures by remapping the customer's public IP addresses to any resource instance associated with the customer's account. The customer IP addresses, for example, enable a customer to engineer around problems with the customer's resource instances or software by remapping customer IP addresses to replacement resource instances.

FIG. 10 is a block diagram of an example provider network that provides a storage service and a hardware virtualization service to customers, according to some embodiments. Hardware virtualization service 1020 provides multiple computation resources 1024 (e.g., VMs) to customers. The computation resources 1024 may, for example, be rented or leased to customers of the provider network 1000 (e.g., to a customer that implements customer network 1050). Each computation resource 1024 may be provided with one or more local IP addresses. Provider network 1000 may be configured to route packets from the local IP addresses of the computation resources 1024 to public Internet destinations, and from public Internet sources to the local IP addresses of computation resources 1024.

Provider network 1000 may provide a customer network 1050, for example coupled to intermediate network 1040 via local network 1056, the ability to implement virtual computing systems 1092 via hardware virtualization service 1020 coupled to intermediate network 1040 and to provider network 1000. In some embodiments, hardware virtualization service 1020 may provide one or more APIs 1002, for example a web services interface, via which a customer network 1050 may access functionality provided by the hardware virtualization service 1020, for example via a console 1094 (e.g., a web-based application, standalone application, mobile application, etc.). In some embodiments, at the provider network 1000, each virtual computing system 1092 at customer network 1050 may correspond to a computation resource 1024 that is leased, rented, or otherwise provided to customer network 1050.

From an instance of a virtual computing system 1092 and/or another customer device 1090 (e.g., via console 1094), the customer may access the functionality of storage service 1010, for example via one or more APIs 1002, to access data from and store data to storage resources 1018A-1018N of a virtual data store 1016 (e.g., a folder or "bucket", a virtualized volume, a database, etc.) provided by the provider network 1000. In some embodiments, a virtualized data store gateway (not shown) may be provided at the customer network 1050 that may locally cache at least some data, for example frequently-accessed or critical data, and that may communicate with storage service 1010 via one or more communications channels to upload new or modified data from a local cache so that the primary store of data (virtualized data store 1016) is maintained. In some embodiments, a user, via a virtual computing system 1092 and/or on another customer device 1090, may mount and access virtual data store 1016 volumes via storage service 1010 acting as a storage virtualization service, and these volumes may appear to the user as local (virtualized) storage 1098.

While not shown in FIG. 10, the virtualization service(s) may also be accessed from resource instances within the provider network 1000 via API(s) 1002. For example, a customer, appliance service provider, or other entity may access a virtualization service from within a respective virtual network on the provider network 1000 via an API 1002 to request allocation of one or more resource instances within the virtual network or within another virtual network.

In some embodiments, a system that implements a portion or all of the techniques described herein may include a general-purpose computer system that includes or is configured to access one or more computer-accessible media, such as computer system 1100 illustrated in FIG. 11. In the illustrated embodiment, computer system 1100 includes one or more processors 1110 coupled to a system memory 1120 via an input/output (I/O) interface 1130. Computer system 1100 further includes a network interface 1140 coupled to I/O interface 1130. While FIG. 11 shows computer system 1100 as a single computing device, in various embodiments a computer system 1100 may include one computing device or any number of computing devices configured to work together as a single computer system 1100.

In various embodiments, computer system 1100 may be a uniprocessor system including one processor 1110, or a multiprocessor system including several processors 1110 (e.g., two, four, eight, or another suitable number). Processors 1110 may be any suitable processors capable of executing instructions. For example, in various embodiments, processors 1110 may be general-purpose or embedded processors implementing any of a variety of instruction set architectures (ISAs), such as the x86, ARM, PowerPC, SPARC, or MIPS ISAs, or any other suitable ISA. In multiprocessor systems, each of processors 1110 may commonly, but not necessarily, implement the same ISA.

System memory 1120 may store instructions and data accessible by processor(s) 1110. In various embodiments, system memory 1120 may be implemented using any suitable memory technology, such as random-access memory (RAM), static RAM (SRAM), synchronous dynamic RAM (SDRAM), nonvolatile/Flash-type memory, or any other type of memory. In the illustrated embodiment, program instructions and data implementing one or more desired functions, such as those methods, techniques, and data described above are shown stored within system memory 1120.

In one embodiment, I/O interface 1130 may be configured to coordinate I/O traffic between processor 1110, system memory 1120, and any peripheral devices in the device, including network interface 1140 or other peripheral interfaces. In some embodiments, I/O interface 1130 may perform any necessary protocol, timing or other data transformations to convert data signals from one component (e.g., system memory 1120) into a format suitable for use by another component (e.g., processor 1110). In some embodiments, I/O interface 1130 may include support for devices attached through various types of peripheral buses, such as a variant of the Peripheral Component Interconnect (PCI) bus standard or the Universal Serial Bus (USB) standard, for example. In some embodiments, the function of I/O interface 1130 may be split into two or more separate components, such as a north bridge and a south bridge, for example. Also, in some embodiments some or all of the functionality of I/O interface 1130, such as an interface to system memory 1120, may be incorporated directly into processor 1110.

Network interface 1140 may be configured to allow data to be exchanged between computer system 1100 and other devices 1160 attached to a network or networks 1150, such as other computer systems or devices as illustrated in FIG. 1, for example. In various embodiments, network interface 1140 may support communication via any suitable wired or wireless general data networks, such as types of Ethernet network, for example. Additionally, network interface 1140 may support communication via telecommunications/telephony networks such as analog voice networks or digital fiber communications networks, via storage area networks (SANs) such as Fibre Channel SANs, or via I/O any other suitable type of network and/or protocol.

In some embodiments, a computer system 1100 includes one or more offload cards 1170 (including one or more processors 1175, and possibly including the one or more network interfaces 1140) that are connected using an I/O interface 1130 (e.g., a bus implementing a version of the Peripheral Component Interconnect Express (PCI-E) standard, or another interconnect such as a QuickPath interconnect (QPI) or UltraPath interconnect (UPI)). For example, in some embodiments the computer system 1100 may act as a host electronic device (e.g., operating as part of a hardware virtualization service) that hosts compute instances, and the one or more offload cards 1170 execute a virtualization manager that can manage compute instances that execute on the host electronic device. As an example, in some embodiments the offload card(s) 1170 can perform compute instance management operations such as pausing and/or un-pausing compute instances, launching and/or terminating compute instances, performing memory transfer/copying operations, etc. These management operations may, in some embodiments, be performed by the offload card(s) 1170 in coordination with a hypervisor (e.g., upon a request from a hypervisor) that is executed by the other processors 1110A-1110N of the computer system 1100. However, in some embodiments the virtualization manager implemented by the offload card(s) 1170 can accommodate requests from other entities (e.g., from compute instances themselves), and may not coordinate with (or service) any separate hypervisor.

In some embodiments, system memory 1120 may be one embodiment of a computer-accessible medium configured to store program instructions and data as described above. However, in other embodiments, program instructions and/or data may be received, sent, or stored upon different types of computer-accessible media. Generally speaking, a computer-accessible medium may include non-transitory storage media or memory media such as magnetic or optical media, e.g., disk or DVD/CD coupled to computer system 1100 via I/O interface 1130. A non-transitory computer-accessible storage medium may also include any volatile or non-volatile media such as RAM (e.g., SDRAM, double data rate (DDR) SDRAM, SRAM, etc.), read only memory (ROM), etc., that may be included in some embodiments of computer system 1100 as system memory 1120 or another type of memory. Further, a computer-accessible medium may include transmission media or signals such as electrical, electromagnetic, or digital signals, conveyed via a communication medium such as a network and/or a wireless link, such as may be implemented via network interface 1140.

Various embodiments discussed or suggested herein can be implemented in a wide variety of operating environments, which in some cases can include one or more user computers, computing devices, or processing devices which can be used to operate any of a number of applications. User or client devices can include any of a number of general-purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially available operating systems and other known applications for purposes such as development and database management. These devices also can include other electronic devices, such as dummy terminals, thin-clients, gaming systems, and/or other devices capable of communicating via a network.

Most embodiments utilize at least one network that would be familiar to those skilled in the art for supporting communications using any of a variety of widely-available protocols, such as Transmission Control Protocol/Internet Protocol (TCP/IP), File Transfer Protocol (FTP), Universal Plug and Play (UPnP), Network File System (NFS), Common Internet File System (CIFS), Extensible Messaging and Presence Protocol (XMPP), AppleTalk, etc. The network(s) can include, for example, a local area network (LAN), a wide-area network (WAN), a virtual private network (VPN), the Internet, an intranet, an extranet, a public switched telephone network (PSTN), an infrared network, a wireless network, and any combination thereof.

In embodiments utilizing a web server, the web server can run any of a variety of server or mid-tier applications, including HTTP servers, File Transfer Protocol (FTP) servers, Common Gateway Interface (CGI) servers, data servers, Java servers, business application servers, etc. The server(s) also may be capable of executing programs or scripts in response requests from user devices, such as by executing one or more Web applications that may be implemented as one or more scripts or programs written in any programming language, such as Java®, C, C# or C++, or any scripting language, such as Perl, Python, PHP, or TCL, as well as combinations thereof. The server(s) may also include database servers, including without limitation those commercially available from Oracle (R), Microsoft (R), Sybase (R), IBM (R), etc. The database servers may be relational or non-relational (e.g., "NoSQL"), distributed or non-distributed, etc.

Environments disclosed herein can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and/or at least one output device (e.g., a display device, printer, or speaker). Such a system may also include one or more storage devices, such as disk drives, optical storage devices, and solid-state storage devices such as random-access memory (RAM) or read-only memory (ROM), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, Electrically Erasable Programmable Read-Only Memory (EEPROM), flash memory or other memory technology, Compact Disc-Read Only Memory (CD-ROM), Digital Versatile Disk (DVD) or other optical storage, magnetic cassettes, magnetic tape, magnetic disk storage or other magnetic storage devices, or any other medium which can be used to store the desired information and which can be accessed by a system device. Based on the disclosure and teachings provided herein, a person of ordinary skill in the art will appreciate other ways and/or methods to implement the various embodiments.

In the preceding description, various embodiments are described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Bracketed text and blocks with dashed borders (e.g., large dashes, small dashes, dot-dash, and dots) are used herein to illustrate optional operations that add additional features to some embodiments. However, such notation should not be taken to mean that these are the only options or optional operations, and/or that blocks with solid borders are not optional in certain embodiments.

V. Immunogenic Composition

The invention further relates to personalized (i.e., subject-specific) immunogenic compositions (e.g., a cancer vaccine) comprising one or more tumor-specific antigens selected using the methods described herein. Such immunogenic compositions can be formulated according to standard procedures in the art. The immunogenic composition is capable of raising a specific immune response.

The immunogenic composition can be formulated so that the selection and number of tumor-specific neoantigens is tailored to the subject's particular cancer. For example, the selection of the tumor-specific neoantigens can be dependent on the specific type of cancer, the stage of the cancer, the immune status of the subject, and the MHC-type of the subject.

The immunogenic composition can comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more tumor-specific neoantigens. The immunogenic composition can contain about 10-20 tumor-specific neoantigens, about 10-30 tumor-specific neoantigens, about 10-40 tumor-specific neoantigens, about 10-50 tumor-specific neoantigens, about 10-60 tumor-specific neoantigens, about 10-70 tumor-specific neoantigens, about 10-80 tumor-specific neoantigens, about 10-90 tumor-specific neoantigens, or about 10-100 tumor-specific neoantigens. Preferably, the immunogenic composition comprises at least about 10 tumor-specific neoantigens or at least about 20 tumor-specific neoantigens.

The immunogenic composition can further comprise natural or synthetic antigens. The natural or synthetic antigens can increase the immune response. Exemplary natural or synthetic antigens include, but are not limited to, pan-DR epitope (PADRE) and tetanus toxin antigen.

The immunogenic composition can be in any form, for example a synthetic long peptide, RNA, DNA, a cell, a dendritic cell, a nucleotide sequence, a polypeptide sequence, a plasmid, or a vector.

Tumor-specific neoantigens can also be included in viral vector-based vaccine platforms, such as vaccinia, fowlpox, self-replicating alphavirus, maraba virus, adenovirus (See, e.g., Tatsis et al., Molecular Therapy, 10:616-629 (2004)), or lentivirus, including, but not limited to, second, third or hybrid second/third generation lentivirus and recombinant lentivirus of any generation designed to target specific cell types or receptors (See, e.g., Hu et al., Immunol Rev., 239(1): 45-61 (2011), Sakma et al, Biochem J., 443(3):603-18 (2012)). Dependent on the packaging capacity of the above-mentioned viral vector-based vaccine platforms, this approach can deliver one or more nucleotide sequences that encode one or more tumor-specific neoantigen peptides. The sequences may be flanked by non-mutated sequences, may be separated by linkers or may be preceded with one or more sequences targeting a subcellular compartment (See, e.g., Gros et al., Nat Med., 22 (4):433-8 (2016), Stronen et al., Science., 352(6291): 1337-1341 (2016), Lu et al., Clin Cancer Res., 20(13):3401-3410 (2014)). Upon introduction into a host, infected cells express the one or more tumor-specific neoantigens, and thereby elicit a host immune (e.g., CD8+ or CD4+) response against the one or more tumor-specific neoantigens. Vaccinia vectors and methods useful in immunization protocols are described in, e.g., U.S. Pat. No. 4,722,848. Another vector is BCG (Bacille Calmette Guerin). BCG vectors are described in Stover et al. (Nature 351:456-460 (1991)). A wide variety of other vaccine vectors useful for therapeutic administration or immunization of neoantigens that will be apparent to those skilled in the art from the description herein may also be used.

The immunogenic composition can contain individualized components, according to the personal needs of the particular subject.

The immunogenic composition described herein can further comprise an adjuvant. Adjuvants are any substance whose admixture into an immunogenic composition increases, or otherwise enhances and/or boosts, the immune response to a tumor-specific neoantigen, but when the substance is administered alone does not generate an immune response to a tumor-specific neoantigen. The adjuvant preferably generates an immune response to the neoantigen and does not produce an allergy or other adverse reaction. It is contemplated herein that the immunogenic composition can be administered before, together, concomitantly with, or after administration of the immunogenic composition.

Adjuvants can enhance an immune response by several mechanisms including, e.g., lymphocyte recruitment, stimulation of B and/or T cells, and stimulation of macrophages. When an immunogenic composition of the invention comprises adjuvants or is administered together with one or more adjuvants, the adjuvants that can be used include, but are not limited to, mineral salt adjuvants or mineral salt gel adjuvants, particulate adjuvants, microparticulate adjuvants, mucosal adjuvants, and immunostimulatory adjuvants. Examples of adjuvants include, but are not limited to, aluminum salts (alum) (such as aluminum hydroxide, aluminum phosphate, and aluminum sulfate), 3 De-O-acylated monophosphoryl lipid A (MPL) (see, GB 2220211), MF59 (Novartis), AS03 (Glaxo SmithKline), AS04 (Glaxo SmithKline), polysorbate 80 (Tween 80; ICL Americas, Inc.), imidazopyridine compounds (see, International Application No. PCT/US2007/064857, published as International Publication No. WO2007/109812), imidazoquinoxaline compounds (see, International Application No. PCT/US2007/064858, published as International Publication No. WO2007/109813) and saponins, such as QS21 (see, Kensil et al, in Vaccine Design: The Subunit and Adjuvant Approach (eds. Powell & Newman, Plenum Press, NY, 1995); U.S. Pat. No. 5,057,540). In some embodiments, the adjuvant is Freund's adjuvant (complete or incomplete). Other suitable adjuvants are oil in water emulsions (such as squalene or peanut oil), optionally in combination with immune stimulants, such as monophosphoryl lipid A (see, Stoute et al, N. Engl. J. Med. 336, 86-91 (1997)).

CpG immunostimulatory oligonucleotides have also been reported to enhance the effects of adjuvants in a vaccine setting. Other TLR binding molecules, such as RNA binding TLR 7, TLR 8 and/or TLR 9, may also be used.

Other examples of useful adjuvants include, but are not limited to, chemically modified CpGs (e.g. CpR, Idera), Poly (I:C) (e.g. polyi:CI2U), poly ICLC, non-CpG bacterial DNA or RNA as well as immunoactive small molecules and antibodies such as cyclophosphamide, sunitmib, bevacizumab, Celebrex (celecoxib), NCX-4016, sildenafil, tadalafil, vardenafil, sorafinib, XL-999, CP-547632, pazopamb, ZD2171, AZD2171, ipilimumab, tremelimumab, and SC58175, which may act therapeutically and/or as an adjuvant. In embodiments, Poly ICLC is a preferable adjuvant.

The immunogenic compositions can comprise one or more tumor-specific neoantigens described herein alone or together with a pharmaceutically acceptable carrier. Suspensions or dispersions of one or more tumor-specific neoantigens, especially isotonic aqueous suspensions, dispersions, or amphiphilic solvents can be used. The immunogenic compositions may be sterilized and/or may comprise excipients, e.g., preservatives, stabilizers, wetting agents and/or emulsifiers, solubilizers, salts for regulating osmotic pressure and/or buffers and are prepared in a manner known per se, for example by means of conventional dispersing and suspending processes. In certain embodiments, such dispersions or suspensions may comprise viscosity-regulating agents. The suspensions or dispersions are kept at temperatures around 2° C. to 8° C., or preferentially for longer storage may be frozen and then thawed shortly before use. For injection, the vaccine or immunogenic preparations may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

In certain embodiments, the compositions described herein additionally comprise a preservative, e.g., the mercury derivative thimerosal. In a specific embodiment, the pharmaceutical compositions described herein comprise 0.001% to 0.01% thimerosal. In other embodiments, the pharmaceutical compositions described herein do not comprise a preservative.

An excipient can be present independently of an adjuvant. The function of an excipient can be, for example, to increase the molecular weight of the immunogenic composition, to increase activity or immunogenicity, to confer stability, to increase the biological activity, or to increase serum-half life. An excipient can also be used to aid presentation of the one or more tumor-specific neoantigens to T-cells (e.g., CD4+ or CD8+ T-cells). The excipient can be a carrier protein such as, but not limited to, keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier is generally a physiologically acceptable carrier acceptable to humans and safe. Alternatively, the carrier can be dextran, for example sepharose.

Cytotoxic T-cells recognize an antigen in the form of a peptide bound to an MHC molecule, rather than the intact foreign antigen itself. The MHC molecule is located at the cell-surface of an antigen presenting cell. Thus, an activation of cytotoxic T-cells is possible if a trimeric complex of peptide antigen, MHC molecule, and antigen-presenting cell (APC) is present. It may enhance the immune response if not only the one or more tumor-specific antigens are used for activation of cytotoxic T-cells, but if additional APCs with the respective MHC molecule are added. Therefore, in some embodiments an immunogenic composition additionally contains at least one APC.

The immunogenic composition can comprise an acceptable carrier (e.g., an aqueous carrier). A variety of aqueous carriers can be used, e.g., water, buffered water, 0.9% saline, 0.3% glycine, hyaluronic acid and the like. These compositions can be sterilized by conventional, well known sterilization techniques, or can be sterile filtered. The resulting aqueous solutions can be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Neoantigens can also be administered via liposomes, which target them to a particular cell tissue, such as lymphoid tissue. Liposomes are also useful in increasing half-life. Liposomes include emulsions, foams, micelles, insoluble monolayers, liquid crystals, phospholipid dispersions, lamellar layers and the like. In these preparations the neoantigen to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired neoantigen can be directed to the site of lymphoid cells, where the liposomes then deliver the selected immunogenic compositions. Liposomes can be formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., An. Rev. Biophys. Bioeng. 9; 467 (1980), U.S. Pat. Nos. 4,235,871, 4,501,728, 4,501,728, 4,837,028, and 5,019,369.

For targeting to the immune cells, a ligand to be incorporated into the liposome can include, e.g., antibodies or fragments thereof specific for cell-surface determinants of the desired immune system cells. A liposome suspension can be administered intravenously, locally, topically, etc. in a dose which varies according to, inter alia, the manner of administration, the peptide being delivered, and the stage of the disease being treated.

An alternative method for targeting immune cells, components of the immunogenic composition, such as an antigen (i.e., tumor-specific neoantigen), ligand, or adjuvant (e.g., TLR) can be incorporated into an poly (lactic-co-glycolic) microspheres. The poly (lactic-co-glycolic) microspheres can entrap components of the immunogenic composition as an endosomal delivery device.

For therapeutic or immunization purposes, nucleic acids encoding a tumor-specific neoantigen described herein can also be administered to the subject. A number of methods are conveniently used to deliver the nucleic acids to the subject. For instance, the nucleic acid can be delivered directly, as "naked DNA". This approach is described, for instance, in Wolff et al., Science 247:1465-1468 (1990), as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles. Approaches for delivering nucleic acid sequences can include viral vectors, mRNA vectors, and DNA vectors with or without electroporation. The nucleic acids can also be delivered complexed to cationic compounds, such as cationic lipids.

The immunogenic compositions provided herein can be administered to the subject by, including but not limited to, oral, intradermal, intratumoral, intramuscular, intraperitoneal, intravenous, topical, subcutaneous, percutaneous, intranasal and inhalation routes, and via scarification (scratching through the top layers of skin, e.g., using a bifurcated needle). The immunogenic composition can be administered at the tumor site to induce a local immune response to the tumor.

The dosage of the one or more tumor-specific neoantigens may depend upon the type of composition and upon the subject's age, weight, body surface area, individual condition, the individual pharmacokinetic data, and the mode of administration.

Also disclosed herein is a method of manufacturing an immunogenic composition comprising one or more tumor-specific neoantigens selected by performing the steps of the methods disclosed herein. An immunogenic composition as described herein can be manufactured using methods known in the art. For example, a method of producing a tumor-specific neoantigen or a vector (e.g., a vector including at least one sequence encoding one or more tumor-specific neoantigens) disclosed herein can include culturing a host cell under conditions suitable for expressing the neoantigen or vector, wherein the host cell comprises at least one polynucleotide encoding the neoantigen or vector, and purifying the neoantigen or vector. Standard purification methods include chromatographic techniques, electrophoretic, immunological, precipitation, dialysis, filtration, concentration, and chromatofocusing techniques.

Host cells can include a Chinese Hamster Ovary (CHO) cell, NSO cell, yeast, or a HEK293 cell. Host cells can be transformed with one or more polynucleotides comprising at least one nucleic acid sequence that encodes one or more tumor-specific neoantigens or vector disclosed herein. In certain embodiments the isolated polynucleotide can be cDNA.

5. EXAMPLES

Example 1.1: Training Data

The models were trained to predict peptide-MHC binding and the probability of endogenous peptide presentation on MHC class I. These are treated as proxies for CD8+ T-cell immunogenicity. Curated peptide-MHC binding affinity data from MHCflurry ("curated_training_data.no_mass_ spec. csv" 1) was used, which contains data from IEDB [1] and Kim et al. [2]. The only processing step performed on this curated dataset was to add peptide source protein/s in order to extract flanking regions and use for our negative sampling methods. The final dataset used for training, after this processing step, is called "curated_training_ data.no_mass_spec.multiple_context.blast.v2.csv." From this dataset only entries with HLA-A/B/C alleles, and peptides of length 8-15 with no post-translational modifications were retained. The target for these samples are either quantitative ('=') or qualitative ('<'/'>') as proposed in MHCflurry-1.2 [3]. The qualitative entries in the MHCflurry curated dataset represent positive-high (<100 nm), positive-intermediate (<1000 nm), positive-low (<5000 nm), or negative (>5000 nm) qualitative values. Additionally, cell-surface peptide presentation datasets were utilized, consisting of cell-surface presented peptides as determined via peptide elution experiments and mass spectrometry, from several sources: Sarkizova et al. [4] dataset, which used mass spectrometry to profile >185,000 peptides eluted from 95 HLA-A, -B, -C and -G mono-allelic cell lines. Mass spectrometry hits, as identified in MHCflurry curated dataset with mass-spectrometry, in which relevant samples were identified by having 'mass spectrometry' value in the 'measurement_source' column. This contains 226,684 MS-identified ligands deposited in IEDB [1] or the SysteMHC Atlas [5], or published by Abelin et al [6].

Additionally, cell-surface presentation data acquired at Fred Hutchinson Cancer Center by stably transfecting HEK293 cells to express secreted human HLA molecules covalently linked to beta-2-microglobulin was used. Then, cellular supernatants were prepared to capture secreted MHC-peptide complexes and analyzed by mass spectrometry. Peptides from purified complexes were reported. The data files are available in the compressed "RolandPeptidePresentationData.zip" file. These data sources all consist of peptide sequences found to be presented on a MHC Class I molecule associated with a specific HLA allele. For our final presentation dataset ("mass_spec_data.multiple_context.blast.allele_supertypes.v3.csv," samples from all mentioned sources containing HLA-A/B/C alleles and peptide source protein/s were merged in order to extract flanking regions and use for negative sampling methods. Near-duplicate "extension" samples were also filtered out, as samples with same allele and same peptide only with a single additional amino acid at either edge were considered to be a duplicate, caused by mass spectrometry measurement inaccuracy. Samples (peptide-MHC pairs) that appear in the immunogenicity evaluation data were also filtered out from both the affinity and presentation datasets, to verify that the evaluation sets are completely "held-out" and not seen by the model, in the training phase, at all.

These datasets (affinity and presentation) were randomly split into train and validation splits before training new models. For each allele we randomly sample $N_{bai}$ peptides from binding affinity samples with the i-th allele, and $N_{pi}$ peptides from presentation samples with the i-th allele. Where $N_{bai}$=min (0.25*|unique affinity peptides |i, 100) and $N_{pi}$=min (0.25*|unique presentation peptides|$_i$, 100).

For each allele, these sampled peptides (union of sampled ones from both datasets) are considered as the held-out validation set, and all samples containing these peptides are removed from the training set and used only for validation. The validation set is used for determining early stopping of model training if validation loss does not improve in over N consecutive epochs. N=20 was set in all of the experiments. When training multiple similar models, for ensemble/model-selection purposes, we use different train-validation splits.

Human rhinovirus (HR) data was included in our data as negatives from ICS applied to 1600 HRV 15mers constructed from HRV-1A, HRV-B, HRV-C mosaics (as described in Fischer et al., (2007), Nature Medicine, 13, 100-106. Specifically, negatives randomly sampled from the ICS results were used for immunogenicity evaluation and were tested as part of the immunogenicity evaluation data. The rest of the HRV samples were treated as negative presentation samples, and they were randomly sampled during training.

Example 1.2: Immunogenicity Evaluation Data

To validate how well predictions from BigMHC 1.0 for peptide-MHC binding affinity and cell-surface peptide presentation translate to predicting T-cell immunogenicity, a T-cell immunogenicity dataset was created, the BigMHC machine learning models were tested and validated. The reported peptide-MHC pairs from the CTL/CD8+ epitope summary table in the HIV molecular immunology database and the reported CTL epitope summary table in the HCV immunology database were used. These tables provide experimentally-verified HIV/HCV CTL/CD8+ epitopes.

All of these samples were in the positive immunogenicity class. In order to obtain peptide-MHC samples that have negative immunogenicity as well, the experiments from which the positive pairs originated we manually reviewed. It was found that while the negative findings were not reported, some of them can be reconstructed from positive findings. Specifically, many experiments tested all possible peptide-MHC pair combinations for a given set of peptides and a given set of HLA alleles, which are referred to as the Matrix method. From positive findings, we were able to extract the reported peptides and alleles and conclude that, at least (there could be additional negatives that we miss as if a peptide/allele is negative within all possible pairing it will not be reported), all possible peptide-MHC paired combinations within them were tested in the experiments. Given this list of tested peptide-MHC pairs, it can be concluded that any pair on this list that was not reported as positive is in fact negative. 31 of the largest experiments (with largest amount of tested samples, |unique alleles|× |unique peptides|) were reviewed, to verify whether the Matrix method was used, out of which 18 used this method. From experiments using other methods, we negative samples were not inferred.

For the remaining, smaller, experiments it was assumed that the Matrix method was used, and all negatives were extracted, unless a sample was reported as positive in a different experiment, in which case we assumed it to be positive. Only HLA-A/B/C alleles were retained, and peptides with length 8-15.

In addition to the data described above, we add positive immunogenicity samples reported in IEDB (Vita et al., (2019), Nucleic acids research, 47, D339-D343.) and additional randomly sampled HRV negative samples. HRV negatives are sampled for alleles with a relatively low positive: negative sample ratio. We consider the ideal ratio as 1:100, and when possible (we do not have HRV samples for all alleles) sample HRV negatives until we reach approximately this ratio. Following this balancing procedure, we filter out all samples of alleles with a ratio smaller than 1:5.

Following this procedure, 2,985 positive and 68,469 negative sample pairs were obtained, covering 110 HLA alleles and 1,416 unique peptides.

This immunogenicity dataset was split into two sets-a validation set 6, for tuning our model's hyper-parameters and making additional configuration choices, and a test set 7 on which we performed our final benchmarking.

Example 1.3: Data Analysis

To better visualize and understand the distribution of the data the following figures were plotted.

Peptide length: FIG. 2B shows the distribution of peptide lengths across all three datasets.

Peptide diversity: the similarity between two peptides are referred to as the number of overlapping amino acids with the best possible alignment. In FIG. 2A, for each similarity threshold, the rate of peptides which have no partner peptide with similarity greater than the given threshold was computed. For this analysis, only unique peptides were taken into account, duplicate peptide were ignored within each dataset. Specifically, the affinity dataset consisted of 35,467 unique peptides out of overall 158,001 samples (22.45%), the presentation dataset consisted of 265,236 unique peptides out of overall 384,812 samples (68.93%) and the immunogenicity dataset consisted of 1416 unique peptides out of the overall 71,474 samples (1.98%).

Target distributions: the distribution of targets, and imbalance between them, differed between the different datasets: Binding affinity—the peptide-MHC binding affinity dataset consisted of a mixture of quantitative and qualitative targets. FIG. 3 shows a high level, qualitative, distribution of binding affinity targets. Presentation—the cell-surface peptide presentation dataset was binary, and our dataset consisted of only positive samples. During training, in the beginning of each epoch, we applied negative sample mining to generate a corresponding negative sample for each positive one. Immunogenicity—the T-cell immunogenicity dataset was binary, yet it was highly unbalanced, and consisted of 2,985 positive and 68,469 negative peptide-MHC pairs.

Sample distribution per-supertype—To better visualize and understand the underlying allele distribution in the dataset, which is hard to visualize on a per-allele basis, FIG. 4 shows the distribution of HLA allele supertypes in our dataset samples. The HLA supertype classification determined by Sidney et al. [7] was applied.

Sample distribution per HLA allele—in addition to HLA allele supertype distribution, FIG. 4 also shows the distribution of HLA alleles in each of the dataset's peptide-MHC samples.

Example 1.4: Negative Mining Data During Training

The cell-surface peptide presentation data consists of only "positive" samples, yet they do not provide the negative samples (which cannot be presented on cell-surface) required for training a binary presentation classifier. Hence, in order to train such a classifier, the following strategies for probabilistic negative mining during training were employed:

HLA Allele Shuffling.

Given a positive sample, consisting of a peptide and corresponding HLA allele, the given allele by randomly sampling a different allele which does not belong to the positive allele's supertype/s were replaced. The HLA supertype classification determined by Sidney et al. [7], which assigns each HLA allele to one or two HLA supertypes, was applied. This classification leaves a few HLA alleles unclassified. The unclassified alleles were mapped into 3 additional supertype classes: "Unclassified-A", "Unclassified-B", and "Unclassified-C", according to the corresponding HLA-A/B/C group and treated these groups similarly to the other supertype classes.

Peptide Shuffling.

Given a positive sample, consisting of a peptide and corresponding HLA allele, the given peptide was replaced with a randomly sampled amino-acid subsequence, of the same length, from the peptide's source protein. In addition, following the method in MHCflurry-1.6 [8], the affinity training dataset was also augmented to include random peptides, sampled from amino-acid data distribution, with qualitative weak affinity targets (>20,000 nM). The length of these random peptides was determined in such a way that enforces an equal number of non-binding data points, per peptide length, for each allele.

HRV Negative Sampling.

We randomly sample from the negative HRV data (excluding samples used for immunogenicity evaluation). The underlying assumption here is that, in most cases, negative immunogenicity will be caused by negative cell-surface presentation, hence it can be assumed during training (although cases with positive presentation and negative immunogenicity exist).

Example 1.5: Cross-Task Target Inferring

For the sake of joint, multi-task, training all training samples from both the binding affinity and presentation datasets were used. However, for each sample only a single known target (as opposed to two tasks) from the corresponding dataset it originated was known. To mitigate this issue (and be able to better leverage multi task training), targets from each task to the other were inferred, by assuming that samples that present on cell-surface (positive presentation) will also have high binding affinity values and samples with poor binding affinity values will not be presented (negative presentation). Specifically, for every positive presentation sample we infer a qualitative high affinity target (<500 nM), and for samples with poor binding affinity measurements (>5000 nM) a negative presentation target was inferred. The rest of the "missing targets" (ones that we cannot infer) are simply ignored (masked out) during training by assigning a sample-weight of zero (only for the task with missing target).

Example 1.6: Self-Distillation

Using the BigMHC predictor, we extracted binding affinity and presentation estimation for various samples and added these samples with their corresponding "weak" labels to the training dataset. We performed this self-distillation process in two scenarios:

1. Multi-Allelic Mass Spec Data. We used The MULTI-ALLELIC OLD dataset, as described in MHCflurry-2.0, which contains >200K positive mass spec hits. We utilized BigMHC-1.3.1 predictions to determine which of the alleles is the one responsible for the hit. First, we filtered out any multi-allelic hit with a known positive presenter from our presentation training data. Second, we selected the allele with highest presentation probability and keep that sample only if the presentation probability is higher than some threshold (0.5) and binding affinity is below a certain threshold (5000 nM).

2. Positive Presenters. For every positive presenter in our training data (after performing the above step), with unknown binding affinity, we estimated the binding affinity based on BigMHC-1.3.1 predictions. We added all samples with predicted binding affinity below 5000 nM to the binding affinity training data.

Example 2.1: Sequence Representations

Each HLA allele was represented by a pseudo-sequence of 49 amino-acids, as used in MHCflurry-1.4. This pseudo-sequence encoding uses amino acids at 49 selected positions determined by multiple sequence alignment of a large number of MHC class-I alleles across species. The HLA allele pseudo-sequence representations are available in the "allele_sequences.csv" file. In addition, the peptide padding and encoding method from O'Donnell et al. [3] was utilized to represent peptides of amino acid length 8-15 using a fixed length encoding designed to preserve the positionality of the residues that make the most important stabilizing contacts with the MHC. These "anchor positions" occur toward the beginning or end of the peptide for most alleles. Peptides are represented as length-15 sequences, in which missing residues are filled with an 'X' character, effectively a 21st amino acid. The first and last four residues in the peptide map to the first and last four positions in the representation. The middle seven residues are filled as needed: an 8-mer leaves all middle positions as an X, whereas a 15-mer fills all positions. In this way, the positions most likely to contain anchor residues are consistently mapped to the same positions in the representation. The peptide's flanking regions were also encoded, considering 5 amino acids per side, which are concatenated at the encoded peptide's edges respectively.

As opposed to O'Donnell et al. [3], which use a fixed amino acid embedding based on the BLOSUM62 substitution matrix, a trainable embedding layer was used, which is jointly trained in an end-to-end manner with the rest of our neural network. This embedding layer encodes every amino acid, both in the encoded peptide or allele pseudo-sequence, into a 16-dimensional vector.

Example 2.2: Flanking Regions

For each peptide sequence, all instances where this sequence is a subset of a longer protein sequence present in the UniProt dataset [9] was identified. 3 UniProt files were searched: (1) UniProt human proteomes data set, "UP000005640_9606.fasta," (2) complete UniProtKB/Swiss-Prot data set, "uniprot_sprot.fasta," (3) additional sequences of the UniProtKB/Swiss-Prot data set that represent all annotated splice variants, "uniprot_sprot_varsplic.fasta," and (4) additional sequences from the netMHCpan-4.0 immunogenicity datasets, both CD8 ("CD8_epitopes_netMHCpan.fas") and CD4 ("CD4_epitopes_netMHCIIpan.fsa") were downloaded.

Each of the longer sequences are called "parent sequences". Each peptide was associated with one or more "flanking regions" of length 10, which are the 5 amino acids in each of the peptide's parent sequence immediately preceding and the 5 amino acids immediately following the peptide sequence. All unique combinations of flanking regions were saved to a file and a weight for each of them that is inversely proportional to the number of unique sequences for each peptide was defined. These weights were used as sample-weights during training, in order to let the network, learn from all possible variations, yet not put more emphasis on peptides with large number of variations. For peptides with no exact matches, we utilized BLAST10 to the find the closest matching peptide and used it's corresponding "parent sequence" to extract the relevant flanking regions.

Example 2.3: Self-Supervised Pre-Training

We utilized large protein databases to pre-train our model and learn good initial sequence representations. Using a subset of 25M proteins from the Uniparc database, we trained the peptide-transformer model on the two following tasks as inspired by BERT pretraining:
1. Masked-Language-Modeling. We randomly selected 0.15 of the tokens to be considered "masked-out" and trained a token classification head which tries to predict the original token (based on all other tokens) using cross-entropy loss. For the model input the "masked out" tokens are sometimes replaced randomly (10%), sometimes left unchanged (10%) and sometimes replaced by a masking token (80%).
2. Next-Peptide-Prediction. In the pre-training phase, our input sequence was a concatenation of two peptide sequences (as opposed to concatenation of peptide and allele sequences in the main training phase). The sequences were separated via a special separation token (<SEP>) and have different segment index and embedding (the segment sequence is an additional input to the network, simply indicating whether each token belongs to first-sequence, second-sequence or special token. Then the embedding of the segment index is added to the token and positions embeddings). We trained a classifier, over the output of the <CLS> token, to predict whether the 2nd peptide is the next occurring peptide (after the 1st one) in the protein or not. The peptides either come from two consecutive, same length, peptides from a human protein or are sampled randomly from different proteins.

Example 2.3 Training Objective and Multi-Task Loss

Our neural network was trained jointly to predict both peptide-MHC binding affinity and cell-surface peptide presentation. As done by O'Donnell et al. [3], we utilized a variation of mean square error (MSE) loss function, denoted by LBA-MSE, whereby measurements which are associated with an inequality, (>) or (<), contribute to the loss only when the inequality is violated, for handling both quantitative and qualitative peptide-MHC binding affinity measurements in the dataset. The exact expression is outlined in Scheme 1 and Scheme 2.

For the binary classification task of cell-surface peptide presentation, we utilized the focal loss [10], denoted by LP-FL, which is a weighted extension of the standard binary cross-entropy loss that gives more emphasis to poorly classified samples. The exact expression is outlined in Scheme 3 (reproduced again below).

$$L_{P\text{-}FL} = \frac{1}{N}\sum_{i=1}^{N}(1 - p_{t_i})^{\gamma}\log p_{t_i},$$

Where the predicted probability of the correct $p_{t_i}$ is:

$$p_{t_i} = \begin{cases} \acute{Y}_i, & Y_i = 1 \\ 1 - \acute{Y}_i, & Y_i = 0 \end{cases}$$

Scheme 3

Here, $\gamma$ is a real parameter, which we set to 1. In the binary case, $Y_i \varepsilon\{0, 1\}$ is the ground truth label and $\breve{Y}_i \varepsilon[0, 1]$ is the predicted presentation probability for the i-th sample. Lin et al. [10] showed focal loss is effective for handling data imbalance; and recent work by Mukhoti et al. [11] also showed it results in better calibrated networks, in comparison to standard cross-entropy loss. The overall objective function is a linear combination of the MSE variant for peptide-MHC binding affinity and binary focal loss for cell-surface peptide presentation, $L={}^{aL}{}_{BA\text{-}MSE}+(1-a)L_{P\text{-}FL}$.

During training, negative sampling strategies mentioned in Example 1.4 we also applied. They were applied at the beginning of each epoch for both the presentation and binding affinity tasks. The negative samples for the validation set were generated once, in the beginning of the first epoch, and were fixed throughout the training process. Inferred targets from each task to the other when possible were also utilized. A sample-weight mechanism was also applied, for each loss term, to give samples different weights based on the amount of flanking region variations, and also masked out samples with missing targets (we masked them out only from the specific task for which the target is unknown). Samples with inferred targets, as explained in Example 1.5, had the same sample-weight for both tasks.

For cell-surface peptide presentation prediction, we train a binary classifier with the binary cross-entropy loss: The presentation objective, denoted by LP-BCE, is:

$$L_{P\text{-}BCE} = -\sum_i \left( Y_i \log \tilde{Y}_i + (1 - Y_i) \log \left(1 - \tilde{Y}_i\right) \right).$$

Scheme 9

The overall objective function is a linear combination of the above training objectives, with predefined weight loss coefficients:

$$L = \hat{\alpha} L_{P\text{-}BCE} + \beta L_{BA\text{-}MSE} + \gamma L_{A\text{-}MLM}. \qquad \text{Scheme 10}$$

During training, we also applied a negative sampling strategy, for each negative we randomly sampled which of the four methods to use. We also defined a hyper-parameter of negative: positive ratio, Nratio, which we used to determine how many negatives to sample per each positive presentation sample. For each sampled negative we assigned a sample-weight of 1/Nratio, thus effectively making sure that the LP-BCE objective is trained on balanced data (overall sample weight of positive and negative training samples is equal).

In addition, during the main training phase we utilized a masked-language-modeling auxiliary objective in which the masked out token are randomly selected only from the peptide's flanking regions. This objective was only applied on natural peptide sequences and hence is ignored for certain types of sampled negatives in which either peptide (e.g. randomly sampled amino-acid sequences) or its context (e.g. HRV negative samples) is "synthetic". We denote this auxiliary loss by $L_{A\text{-}MLM}$.

Example 2.4 Calibration

Recent work by Guo et al. shows that modern neural networks are poorly calibrated. The calibration property is of high importance for us, as in our ranking logic pipeline we used probabilistic computations to make decisions based on the predicted presentation probability. Specifically, in the vaccine design pipeline, given a subject's 6 HLA alleles, we applied the following probabilistic computation to estimate the overall presentation probability for the subject's alleles based on the model's predictions on each single HLA allele:

$$P_{presentation}(\text{peptide} \mid \text{allele}_1, \ldots, \text{allele}_6) =$$

$$1 - \prod_{i=1}^{6} (1 - P_{presentation}(\text{peptide} \mid \text{allele}_i))$$

Scheme 4

These types of computations will be enhanced if our predictors are properly calibrated. Hence, we further calibrated the network's presentation predictions, on the validation set, by fitting a low degree polynomial to the calibration curve. All polynomial coefficients were constrained to be positive to obtain a monotonic increasing function. Lasso linear regression for this task was used. This step was crucial in order to obtain well calibrated presentation probabilities, which are later used in our inference pipeline, however, as the calibration step is monotonic, it does not affect the ranking of peptides for a single allele. In our vaccine design pipeline, we used the calibrated presentation predictions as our best proxy for immunogenicity probability estimation.

Example 2.5 Model Architecture

A. Model Architecture 1

This model's architecture was composed of 3 primary components: sequence processing, peptide-MHC binding affinity prediction, followed by cell-surface peptide presentation prediction. The inputs to our model are the peptide primary sequences, including flanking regions as described above, and the HLA allele pseudo-sequences of length 49 amino acids. The peptide sequence was first encoded into a fixed length vector, afterwards all amino-acid sequences were encoded using a shared, d-dimensional, amino-acid embedding layer. The embedded sequences were then flattened, to produce a vector representation for each peptide, allele and flanking region. For the peptide-MHC binding affinity prediction component, we concatenated the peptide and HLA allele representations and applied 2 dense layers, of sizes 512 and 256, each followed by an Exponential Linear Unit (ELU) activation and a dropout layer with dropout probability p=0.5. The output of this component is called the "affinity representation". An additional dense linear layer was then used to output the predicted binding affinity logit. Finally, for the cell-surface peptide presentation prediction component, the peptide, flanking region, and HLA allele representations were first concatenated into a single vector. Then a series of 2 fully-connected layers were utilized, with similar configuration as in the peptide-MHC binding affinity prediction component, but the output to the "affinity representation" from above was also concatenated. The output of this component is called the "presentation representation". Afterwards, an additional linear, dense layer was added to predict the cell-surface peptide presentation probability logit.

B. Model Architecture 1

The model is composted of the three components: 1. Sequence embedding, 2. Self-attention transformer layers, and 3. Prediction heads.

1. Sequence Embedding—The model received as input 2 sequences: 1) an amino-acid sequence (concatenation of allele pseudo-sequence and peptide with flanking regions). 2) A segment identifier sequence, which "informs" the model to which segment each amino-acid belongs (allele, peptide, context, and special tokens). FIG. 12 demonstrates the composition of the token and segment input sequences. Each token of the sequence is represented by an addition of the aa embedding, a learned positional embedding, and the segment embedding.

$$X = aa\_\text{embed}(x) + \text{pos\_embed}(x) + \text{seg\_embed}(\text{seg}) \qquad \text{Scheme 11}$$

2. Self-attention transformer layers. The embedded sequence was processed with 12 consecutive transformer layers, each containing a Multi-Head self-attention module followed by a feed-forward module (composed of 2 linear layers with GELU activation in between) as illustrated in FIG. 13. Layer normalization is applied in the beginning of each module and residual dropouts of rate p=0.1 are applied at the end of each components before residual connection.

3. Prediction Heads—The model contained the following 3 prediction heads:

Masked-Language-Modeling: the final representation, at each position of the sequence, was fed into the LM prediction head composed of a linear layer (with gelu activation followed by layer normalization) and an additional linear projection (to token vocabulary size) with tied weights to token embedding matrix with an additional learned bias.

Binding-Affinity: the final representation, at the <CLS> token position, was fed into a prediction head composed of: Linear+GELU+LayerNorm+Dropout+Linear.

Presentation: the final representation, at the <CLS> token position, concatenated with the single binding affinity logit, was fed into a prediction head composed of: Linear+GELU+ LayerNorm+Dropout+Linear

Example 2.6 Model Ensembles

The above neural network architecture was used for training 2 types of models: (1) pan-allele, in which all training data is included, and (2) allele-specific, in which training data is partitioned by HLA allele. A separate HLA allele-specific model is trained for each HLA allele with sufficient training data (a criteria of having at least 1K binding affinity and 1K presentation samples in the datasets was utilized).

Both types have the exact same architecture and are trained similarly. They differ only in their training data: the list of supported alleles at inference, and their weight initialization. While pan models are randomly initialized, the allele-specific models are finetuned from the best trained pan model. At inference time, an ensemble of trained models was utilized, which averages predictions for each sample over all models which support the sample's allele.

Example 2.7 Model Selection

Early experimentation showed that often a subset of models, or even a single model, performs better than an ensemble of many models. Hence, we developed the following model selection procedure: 1. For every given model configuration (pan model and allele-specific models for each allele with sufficient training data), we train 10 models with exact training setup only using different folds (train-validation splits). After training is completed, for every model configuration we select the single, best performing, model out of the 10 trained ones, based on our evaluation protocol, using the validation immunogenicity data split. We apply a per-allele hierarchical model selection, in which for every allele (with immunogenicity data for performance validation), we select the best possible configuration out of the following options: a) use allele-specific model only; b) use pan model only; c) use an ensemble of the pan model+allele-specific model and average their predictions.

Example 2.8 Evaluation

In order to evaluate model performance, the T-cell immunogenicity data was utilized to check how well a given trained model manages to rank positive, immunogenic peptide-HLA allele pairs higher than the negative, non-immunogenic ones. Specifically, about the top 20 ranked peptides are of interest as this is, roughly, the amount of peptides desired to manufacture a given vaccine. Given the immunogenicity validation/test set, the model's predictions can be extracted on all samples. With this in mind, 3 common ranking metrics were utilized, which focus on the top-K ranked items, Precision@K, nDCGK, and Reciprocal Rank. The Positive Predictive Value metric was also utilized, which was used in previous work, such as O'Donnell et al. [13]. For each allele, in the immunogenicity validation/test set, all corresponding peptides were separately ranked based on their predicted cell-surface peptide presentation probability or their predicted binding affinity scores, and calculated the Precision@K, nDCGK, Reciprocal Rank, and Positive Predictive Value metrics for each allele.

After computing these metrics over each allele separately, we aggregated them across all HLA alleles by applying a weighted average, in which each allele is weighted by its frequency in the US population. We used allele frequencies for the 4 largest ethical groups in the US [11]. The frequencies derived by these files were further weighted by the frequency of each ethnicity in the US population [12]. Specifically, 0.54 for Euro-Caucasian, 0.22 for Hispanic, 0.17 for African-American and 0.07 for Asian was used. The motivation to weight by allele frequency in population is so that the metric captures (or at least correlate better) with the rate of subjects this method can theoretically be able to help. The population-based frequency weight of HLA alleles in the immunogenicity evaluation set are plotted in FIG. 7. The final metrics, Weighted Precision@K (WP@K), Weighted nDCGK (WnDCGK), Weighted-Reciprocal-Rank (WRR), and Weighted Positive Predictive Value (WPPV) are given by:

$$WP@K = \sum_i \hat{f}_i \frac{|Positive-Samples \cap Top-K-Ranked-Samples|}{\bar{K}_i}$$

$$WnDCG_K = \sum_i \hat{f}_i \frac{DCG_K}{IDCG_K},$$

where $$DCG_K = \sum_{k=1}^{K} \frac{2^{rel_k} - 1}{\log(k+1)},$$

Scheme 5

$rel_k$ is the ground truth relevance of the k-th ranked item, which is in our case the binary immunogenicity label. $IDCG_K$ is the $DCG_K$ score over an ideal, ground-truth based, ranking of reference items.

$$WRR = \sum_i \frac{\hat{f}_i}{rank_i}$$

Scheme 6

Where, $rank_i$ is the rank of the first positive sample in the ranked peptides of the i-th allele.

$$WPPV = \sum_i \hat{f}_i \frac{|Positive-Samples \cap Top-N_i-Ranked-Samples|}{N_i}$$

Scheme 7

Where, Ni is the number of positive samples for the i-th allele. In all metrics, $$\tilde{f}_i = f_i / \Sigma_i f_i \qquad \text{Scheme 8}$$

is the HLA allele frequency weight based on US population statistics, and their values are within [0, 1] range (higher is better). In practice, K=20 was used for WnDCGK metric and for WP@K use Ki=min (20, |Positive-Samples|$_i$), as some alleles have less than 20 positive samples in our evaluation data.

The PPV metric, although informative, does not focus on the top few ranked peptides, which is the region we were mostly interested in. The Reciprocal Rank metric, uses the rank of the first positive item within the ranked peptides, giving high score the higher it is ranked. However, this metric ignores the presence/absence of additional positive peptides in the top ranked items. Since we wanted to make sure we had as many possible positives as possible (as not all presented peptides will also be immunogenic and yield the desired immune response), in our designed vaccine, it was not ideal. The Precision@K metric simply captures the rate of positives within the top K ranked items. However, it does not take into consideration their actual rank within the top K (meaning one positive item ranked first vs. one positive ranked in the K-th place will get the exact same score, which is not ideal). The nDCGK metric takes into consideration both the rate of positives within top K and their corresponding ranks. The normalization factor, by the DCG of the ideal ranking, also diminishes the need to limit K if the number of positives is lower than 20, and also yields values within [0,1] range. However, these scores are still somewhat less interpretable/intuitive in comparison to the precision@K metric.

Example 3.1 Results

Unless stated explicitly otherwise, we trained all of the models with the ADAM optimizer, using 0.001 learning rate and 256 batch size. We set α=0.5, as the loss term coefficient, giving both loss terms equal weight. Early stopping was applied, after 20 epochs with no observed improvement in our validation loss, which is evaluated on a held-out validation set. Both a small L1 regularization factor of 1e-9, and dropouts with a 0.5 drop rate were applied. For all of the models, negative sampling methods, and target inferring were applied. For allele-specific models, where we did not want to replace alleles from positive samples with an allele from different supertype (as we are only interested in samples of a specific allele), we reversed the implementation and put aside (before filtering all data from other alleles) a repository of positive samples with alleles from other supertypes (beside the supertype/s of the specific allele for which we are training) and randomly sampled positive samples from this set, while replacing the "external" allele with the current allele we were training on. For the final predictor a set of the following model types: 1. Pan model, and 2. Allele-specific specific model were trained. Such models were trained only on a subset of alleles with sufficient training data. Specifically, only alleles with at least 1K binding affinity and 1K presentation training samples were trained.

For each type 10 similar models were trained on different train-validation splits, and the best performing model on the immunogenicity validation set was selected. The hierarchical model selection was the applied to determine, for each allele, which model/s to use during inference.

In order to verify whether multi-task training is beneficial in our setting the effect of the loss weight coefficient α was explored. Several pan model 3-fold experiments were performed, with identical setup except for this hyper-parameter, and reported mean WP@K over the immunogenicity test split. Results acquired by both ranking by affinity prediction and ranking by presentation prediction were plotted to capture the full effect. FIG. 7 illustrates clearly that α=0 and α=1, which correspond to presentation-only and affinity-only training respectively, resulting in poorer results in comparison to intermediate values which corresponds to joint training using a weighted combination of both objectives.

To verify our assumption that presentation probability is a good proxy for immunogenicity estimation, a histogram of binned presentation predictions was plotted with the rate of positive immunogenicity samples for each bin. The positive slope, as seen in FIG. 8A, confirmed the $dP_{immunogenicity}/dP_{presentation}>0$, i.e., on average, increasing probability of presentation for a peptide increases the chances it's immunogenic. For comparison, we also explored the equivalent behavior with respect to binding affinity predictions and observe, in FIG. 8B a similar pattern. We also compared performance between our model and other state-of-the-art predictors.

Specifically, we compared performance with MHCflurry-2.0 from O'Donnell et al. and its previous versions. The comparison was done using our evaluation protocol and metrics, the reported numbers were computed over the immunogenicity test split. As can be seen from Table 1, our best predictor significantly outperformed all variants of the MHCflurry-2.0 predictor and previous versions. We can also see that our single pan model outperformed the collection of allele-specific models (which makes sense as they do not support predictions on all alleles), yet the combination of both with the hierarchical model selection provided an additional performance boost.

TABLE 1

Evaluation results the proposed immunogenicity benchmark. Performance comparison between the best predictor and the MHCflurry predictor. Reported metrics are: Weighted Precision@K (WP@K), Weighted nDCGK (WnDCGK), Weighted Reciprocal Rank (WRR) and Weighted Positive Predictive Value (WPPV), in all higher is better.

| Predictor | | WP@K | WnDCG$_{20}$ | WRR | WPPV |
|---|---|---|---|---|---|
| BigMHC-2.0 | Presentation predictor | 0.589 | 0.651 | 0.763 | 0.492 |
| | Affinity predictor | 0.539 | 0.602 | 0.725 | 0.459 |
| BigMHC-1.3 | Presentation predictor | 0.535 | 0.591 | 0.744 | 0.418 |

TABLE 1-continued

Evaluation results the proposed immunogenicity benchmark. Performance comparison between the best predictor and the MHCflurry predictor. Reported metrics are: Weighted Precision@K (WP@K), Weighted nDCGK (WnDCGK), Weighted Reciprocal Rank (WRR) and Weighted Positive Predictive Value (WPPV), in all higher is better.

| Predictor | | WP@K | WnDCG$_{20}$ | WRR | WPPV |
|---|---|---|---|---|---|
| | Affinity predictor | 0.466 | 0.526 | 0.703 | 0.396 |
| MHCflurry-2.0 | Presentation predictor + flanks | 0.421 | 0.501 | 0.627 | 0.343 |
| | Presentation predictor (no flanks) | 0.424 | 0.5 | 0.659 | 0.348 |
| | Affinity predictor | 0.468 | 0.547 | 0.69 | 0.383 |

We additionally compared performance per allele (for all alleles with immunogenicity data to evaluate on) between our best predictor, the "Pan+Allele-Specific–presentation predictor" and MHCflurry-2.0 best predictor, the "pan (+ms)–affinity predictor". The results are presented in Table 2.

TABLE 2

Performance comparison per allele, between the best predictor described herein and MHCflurry-2.0 baseline, the proposed immunogenicity benchmark. Reported metrics are: Precision@K (P@K), nDCG20, Reciprocal Rank (RR) and Positive Predictive Value (PPV), in all higher is better.

| Allele | BigMHC-2.0 | | | | BigMHC-1.3 | | | | MHCflurry-2.0 | | | |
|---|---|---|---|---|---|---|---|---|---|---|---|---|
| | P@K | nDCG$_{20}$ | RR | PPV | P@K | nDCG$_{20}$ | RR | PPV | P@K | nDCG$_{20}$ | RR | PPV |
| HLA- | 0.9 | 0.967 | 1.0 | 0.5 | 0.8 | 0.786 | 0.5 | 0.4 | 0.6 | 0.721 | 1.0 | 0.4 |
| HLA- | 0.0 | 0.256 | 0.0 | 0.0 | 0.0 | 0.387 | 0.2 | 0.0 | 0.0 | 0.500 | 0.3 | 0.0 |
| HLA- | 1.0 | 1.000 | 1.0 | 0.8 | 1.0 | 1.000 | 1.0 | 0.6 | 0.9 | 0.906 | 1.0 | 0.6 |
| HLA- | 0.3 | 0.296 | 0.5 | 0.3 | 0.3 | 0.358 | 0.3 | 0.3 | 0.0 | 0.257 | 0.1 | 0.0 |
| HLA- | 0.2 | 0.356 | 1.0 | 0.2 | 0.2 | 0.368 | 1.0 | 0.2 | 0.2 | 0.233 | 0.2 | 0.2 |
| HLA- | 0.4 | 0.655 | 1.0 | 0.4 | 0.4 | 0.661 | 1.0 | 0.4 | 0.4 | 0.726 | 1.0 | 0.4 |
| HLA- | 1.0 | 1.000 | 1.0 | 1.0 | 1.0 | 1.000 | 1.0 | 1.0 | 0.0 | 0.500 | 0.3 | 0.0 |
| HLA- | 0.0 | 0.000 | 0.0 | 0.0 | 0.0 | 0.000 | 0.0 | 0.0 | 0.0 | 0.500 | 0.3 | 0.0 |
| HLA- | 0.5 | 0.613 | 1.0 | 0.5 | 0.0 | 0.000 | 0.0 | 0.0 | 0.0 | 0.264 | 0.2 | 0.0 |
| HLA- | 0.8 | 0.876 | 1.0 | 0.5 | 0.7 | 0.814 | 1.0 | 0.4 | 0.6 | 0.704 | 1.0 | 0.4 |
| HLA- | 0.9 | 0.913 | 1.0 | 0.7 | 0.7 | 0.777 | 1.0 | 0.4 | 0.6 | 0.644 | 1.0 | 0.4 |
| HLA- | 0.0 | 0.000 | 0.0 | 0.0 | 0.0 | 0.000 | 0.0 | 0.0 | 0.0 | 0.000 | 0.0 | 0.0 |
| HLA- | 0.3 | 0.420 | 1.0 | 0.3 | 0.3 | 0.423 | 1.0 | 0.3 | 0.3 | 0.368 | 0.5 | 0.3 |
| HLA- | 0.4 | 0.443 | 0.5 | 0.4 | 0.5 | 0.584 | 1.0 | 0.4 | 0.5 | 0.542 | 1.0 | 0.3 |
| HLA- | 0.9 | 0.863 | 1.0 | 0.6 | 0.6 | 0.691 | 1.0 | 0.4 | 0.7 | 0.794 | 1.0 | 0.4 |
| HLA- | 0.6 | 0.774 | 1.0 | 0.6 | 0.6 | 0.777 | 1.0 | 0.6 | 0.5 | 0.666 | 1.0 | 0.5 |
| HLA- | 0.7 | 0.802 | 1.0 | 0.7 | 0.7 | 0.869 | 1.0 | 0.7 | 0.5 | 0.747 | 1.0 | 0.5 |
| HLA- | 0.0 | 0.237 | 0.2 | 0.0 | 0.5 | 0.613 | 1.0 | 0.5 | 0.5 | 0.613 | 1.0 | 0.5 |
| HLA- | 0.0 | 0.544 | 0.3 | 0.0 | 0.0 | 0.362 | 0.0 | 0.0 | 1.0 | 1.000 | 1.0 | 1.0 |
| HLA- | 1.0 | 1.000 | 1.0 | 1.0 | 0.0 | 0.500 | 0.3 | 0.0 | 1.0 | 1.000 | 1.0 | 1.0 |
| HLA- | 0.2 | 0.281 | 1.0 | 0.2 | 0.1 | 0.267 | 1.0 | 0.1 | 0.1 | 0.213 | 1.0 | 0.0 |
| HLA- | 0.6 | 0.735 | 1.0 | 0.6 | 0.6 | 0.584 | 0.5 | 0.6 | 0.6 | 0.735 | 1.0 | 0.6 |
| HLA- | 0.2 | 0.175 | 0.2 | 0.2 | 0.1 | 0.106 | 0.2 | 0.1 | 0.2 | 0.177 | 0.2 | 0.1 |
| HLA- | 0.5 | 0.630 | 1.0 | 0.5 | 0.5 | 0.678 | 1.0 | 0.5 | 0.5 | 0.690 | 1.0 | 0.5 |
| HLA- | 0.4 | 0.378 | 0.5 | 0.4 | 0.3 | 0.507 | 1.0 | 0.3 | 0.2 | 0.323 | 0.1 | 0.2 |
| HLA- | 0.2 | 0.442 | 1.0 | 0.2 | 0.2 | 0.493 | 1.0 | 0.2 | 0.3 | 0.511 | 1.0 | 0.3 |
| HLA- | 0.4 | 0.428 | 0.5 | 0.4 | 0.4 | 0.428 | 0.5 | 0.4 | 0.4 | 0.688 | 1.0 | 0.4 |
| HLA- | 0.5 | 0.616 | 0.5 | 0.5 | 0.5 | 0.628 | 1.0 | 0.5 | 0.5 | 0.697 | 0.5 | 0.5 |
| HLA- | 0.1 | 0.289 | 1.0 | 0.1 | 0.1 | 0.148 | 0.5 | 0.1 | 0.2 | 0.280 | 0.5 | 0.2 |
| HLA- | 0.0 | 0.000 | 0.0 | 0.0 | 0.0 | 0.000 | 0.0 | 0.0 | 0.0 | 0.000 | 0.0 | 0.0 |
| HLA- | 0.0 | 0.000 | 0.0 | 0.0 | 0.0 | 0.000 | 0.0 | 0.0 | 0.0 | 0.000 | 0.0 | 0.0 |
| HLA- | 0.7 | 0.776 | 1.0 | 0.6 | 0.4 | 0.551 | 1.0 | 0.4 | 0.5 | 0.628 | 1.0 | 0.5 |
| HLA- | 0.2 | 0.343 | 1.0 | 0.2 | 0.2 | 0.356 | 1.0 | 0.2 | 0.2 | 0.160 | 0.1 | 0.2 |
| HLA- | 0.3 | 0.587 | 1.0 | 0.3 | 0.0 | 0.202 | 0.2 | 0.0 | 0.3 | 0.366 | 0.3 | 0.3 |
| HLA- | 0.1 | 0.413 | 0.3 | 0.1 | 0.1 | 0.408 | 0.3 | 0.1 | 0.0 | 0.351 | 0.1 | 0.0 |
| HLA- | 0.0 | 0.117 | 0.0 | 0.0 | 0.0 | 0.107 | 0.0 | 0.0 | 0.3 | 0.576 | 1.0 | 0.3 |
| HLA- | 0.5 | 0.469 | 0.5 | 0.4 | 0.3 | 0.285 | 0.1 | 0.1 | 0.6 | 0.679 | 1.0 | 0.4 |
| HLA- | 0.9 | 0.967 | 1.0 | 0.6 | 0.9 | 0.935 | 1.0 | 0.6 | 0.7 | 0.700 | 0.5 | 0.5 |
| HLA- | 0.0 | 0.270 | 0.0 | 0.0 | 0.0 | 0.289 | 0.1 | 0.0 | 0.0 | 0.301 | 0.1 | 0.0 |
| HLA- | 0.9 | 0.912 | 1.0 | 0.5 | 0.7 | 0.796 | 1.0 | 0.4 | 0.6 | 0.623 | 1.0 | 0.3 |
| HLA- | 0.4 | 0.656 | 1.0 | 0.4 | 0.3 | 0.567 | 1.0 | 0.3 | 0.2 | 0.346 | 1.0 | 0.2 |
| HLA- | 0.5 | 0.867 | 1.0 | 0.5 | 0.5 | 0.855 | 1.0 | 0.5 | 0.5 | 0.817 | 1.0 | 0.5 |
| HLA- | 0.3 | 0.541 | 1.0 | 0.3 | 0.3 | 0.541 | 1.0 | 0.3 | 0.3 | 0.441 | 1.0 | 0.3 |
| HLA- | 0.6 | 0.723 | 1.0 | 0.6 | 0.6 | 0.723 | 1.0 | 0.6 | 0.4 | 0.648 | 1.0 | 0.4 |

TABLE 2-continued

Performance comparison per allele, between the best predictor described herein and
MHCflurry-2.0 baseline, the proposed immunogenicity benchmark. Reported metrics are:
Precision@K (P@K), nDCG20, Reciprocal Rank (RR) and Positive Predictive Value (PPV),
in all higher is better.

| Allele | BigMHC-2.0 | | | | BigMHC-1.3 | | | | MHCflurry-2.0 | | | |
|---|---|---|---|---|---|---|---|---|---|---|---|---|
| | P@K | nDCG$_{20}$ | RR | PPV | P@K | nDCG$_{20}$ | RR | PPV | P@K | nDCG$_{20}$ | RR | PPV |
| HLA- | 0.0 | 0.631 | 0.5 | 0.0 | 0.0 | 0.631 | 0.5 | 0.0 | 0.0 | 0.500 | 0.3 | 0.0 |
| HLA- | 0.4 | 0.432 | 0.3 | 0.3 | 0.3 | 0.325 | 0.2 | 0.2 | 0.3 | 0.288 | 0.3 | 0.2 |
| HLA- | 0.1 | 0.374 | 1.0 | 0.1 | 0.1 | 0.229 | 0.3 | 0.1 | 0.1 | 0.264 | 0.1 | 0.1 |
| HLA- | 0.5 | 0.635 | 1.0 | 0.5 | 0.5 | 0.609 | 1.0 | 0.5 | 0.4 | 0.524 | 1.0 | 0.4 |
| HLA- | 0.5 | 0.645 | 1.0 | 0.5 | 0.5 | 0.645 | 1.0 | 0.5 | 0.5 | 0.645 | 1.0 | 0.5 |
| HLA- | 0.0 | 0.000 | 0.0 | 0.0 | 0.0 | 0.000 | 0.0 | 0.0 | 0.0 | 0.000 | 0.0 | 0.0 |
| HLA- | 0.0 | 0.083 | 0.1 | 0.0 | 0.0 | 0.079 | 0.1 | 0.0 | 0.1 | 0.137 | 0.3 | 0.1 |
| HLA- | 0.0 | 0.167 | 0.1 | 0.0 | 0.0 | 0.141 | 0.1 | 0.0 | 0.0 | 0.246 | 0.0 | 0.0 |
| HLA- | 0.0 | 0.100 | 0.0 | 0.0 | 0.0 | 0.096 | 0.0 | 0.0 | 0.0 | 0.100 | 0.0 | 0.0 |
| HLA- | 0.5 | 0.662 | 1.0 | 0.3 | 0.5 | 0.670 | 1.0 | 0.3 | 0.6 | 0.702 | 1.0 | 0.3 |
| HLA- | 0.6 | 0.697 | 1.0 | 0.5 | 0.8 | 0.830 | 1.0 | 0.5 | 0.6 | 0.606 | 0.5 | 0.5 |
| HLA- | 0.0 | 0.231 | 0.0 | 0.0 | 0.0 | 0.256 | 0.0 | 0.0 | 0.0 | 0.000 | 0.0 | 0.0 |
| HLA- | 0.5 | 0.452 | 0.3 | 0.5 | 0.5 | 0.454 | 0.5 | 0.5 | 0.5 | 0.626 | 1.0 | 0.5 |
| HLA-B*35:01 | 0.950 | 0.955 | 1.000 | 0.663 | 1.000 | 1.000 | 1.000 | 0.584 | 0.850 | 0.841 | 1.000 | 0.562 |
| HLA- | 0.1 | 0.104 | 0.3 | 0.1 | 0.1 | 0.132 | 0.2 | 0.1 | 0.2 | 0.158 | 0.1 | 0.1 |
| HLA- | 0.1 | 0.133 | 0.2 | 0.1 | 0.1 | 0.122 | 0.1 | 0.1 | 0.1 | 0.076 | 0.1 | 0.1 |
| HLA- | 0.0 | 0.289 | 0.1 | 0.0 | 0.0 | 0.315 | 0.1 | 0.0 | 0.0 | 0.356 | 0.1 | 0.0 |
| HLA- | 0.0 | 0.000 | 0.0 | 0.0 | 0.0 | 0.000 | 0.0 | 0.0 | 0.0 | 0.000 | 0.0 | 0.0 |
| HLA- | 0.1 | 0.454 | 1.0 | 0.1 | 0.1 | 0.268 | 0.5 | 0.1 | 0.1 | 0.371 | 0.5 | 0.1 |
| HLA- | 0.6 | 0.834 | 1.0 | 0.6 | 0.6 | 0.701 | 1.0 | 0.6 | 0.6 | 0.627 | 1.0 | 0.6 |
| HLA- | 0.1 | 0.281 | 1.0 | 0.1 | 0.1 | 0.220 | 1.0 | 0.1 | 0.1 | 0.220 | 1.0 | 0.1 |
| HLA- | 0.0 | 0.334 | 0.1 | 0.0 | 0.0 | 0.182 | 0.2 | 0.0 | 0.0 | 0.167 | 0.1 | 0.0 |
| HLA- | 0.7 | 0.789 | 1.0 | 0.5 | 0.7 | 0.772 | 1.0 | 0.4 | 0.6 | 0.665 | 1.0 | 0.4 |
| HLA- | 0.5 | 0.574 | 0.5 | 0.5 | 0.3 | 0.430 | 0.5 | 0.3 | 0.3 | 0.474 | 1.0 | 0.3 |
| HLA- | 0.5 | 0.911 | 1.0 | 0.5 | 0.5 | 0.888 | 1.0 | 0.5 | 0.5 | 0.839 | 1.0 | 0.5 |
| HLA- | 0.0 | 0.000 | 0.0 | 0.0 | 0.0 | 0.000 | 0.0 | 0.0 | 0.0 | 0.000 | 0.0 | 0.0 |
| HLA- | 0.4 | 0.375 | 0.3 | 0.3 | 0.4 | 0.397 | 0.5 | 0.3 | 0.3 | 0.280 | 0.2 | 0.3 |
| HLA- | 0.1 | 0.095 | 0.2 | 0.1 | 0.2 | 0.253 | 0.1 | 0.2 | 0.5 | 0.561 | 0.5 | 0.5 |
| HLA- | 0.2 | 0.312 | 1.0 | 0.2 | 0.2 | 0.360 | 1.0 | 0.2 | 0.3 | 0.484 | 1.0 | 0.3 |
| HLA- | 0.7 | 0.921 | 1.0 | 0.7 | 0.7 | 0.918 | 1.0 | 0.7 | 0.5 | 0.918 | 1.0 | 0.5 |
| HLA- | 0.5 | 0.606 | 0.3 | 0.5 | 0.5 | 0.690 | 1.0 | 0.5 | 0.5 | 0.651 | 0.5 | 0.5 |
| HLA- | 1.0 | 1.000 | 1.0 | 1.0 | 1.0 | 1.000 | 1.0 | 1.0 | 1.0 | 1.000 | 1.0 | 1.0 |
| HLA- | 0.4 | 0.652 | 1.0 | 0.4 | 0.4 | 0.495 | 0.3 | 0.4 | 0.3 | 0.412 | 0.3 | 0.3 |
| HLA- | 1.0 | 1.000 | 1.0 | 1.0 | 0.0 | 0.631 | 0.5 | 0.0 | 0.0 | 0.431 | 0.2 | 0.0 |
| HLA- | 0.0 | 0.000 | 0.0 | 0.0 | 0.0 | 0.000 | 0.0 | 0.0 | 0.5 | 0.387 | 0.5 | 0.5 |
| HLA- | 0.0 | 0.095 | 0.1 | 0.0 | 0.0 | 0.000 | 0.0 | 0.0 | 0.0 | 0.000 | 0.0 | 0.0 |
| HLA- | 0.0 | 0.343 | 0.2 | 0.0 | 0.3 | 0.402 | 0.3 | 0.3 | 0.0 | 0.343 | 0.2 | 0.0 |
| HLA- | 0.6 | 0.685 | 1.0 | 0.5 | 0.6 | 0.697 | 1.0 | 0.3 | 0.4 | 0.583 | 1.0 | 0.4 |
| HLA- | 0.3 | 0.481 | 1.0 | 0.3 | 0.2 | 0.250 | 0.5 | 0.2 | 0.2 | 0.275 | 1.0 | 0.2 |
| HLA- | 0.3 | 0.274 | 0.3 | 0.2 | 0.3 | 0.224 | 0.1 | 0.2 | 0.2 | 0.194 | 0.1 | 0.2 |
| HLA- | 0.4 | 0.534 | 0.3 | 0.4 | 0.4 | 0.637 | 0.3 | 0.4 | 0.6 | 0.667 | 0.3 | 0.6 |
| HLA- | 0.1 | 0.160 | 0.5 | 0.1 | 0.1 | 0.219 | 0.5 | 0.1 | 0.1 | 0.160 | 0.5 | 0.1 |
| HLA- | 0.0 | 0.291 | 0.0 | 0.0 | 0.0 | 0.000 | 0.0 | 0.0 | 0.0 | 0.171 | 0.0 | 0.0 |
| HLA- | 0.7 | 0.712 | 1.0 | 0.5 | 0.7 | 0.714 | 1.0 | 0.4 | 0.7 | 0.745 | 1.0 | 0.4 |
| HLA- | 0.0 | 0.074 | 0.0 | 0.0 | 0.2 | 0.412 | 1.0 | 0.2 | 0.1 | 0.340 | 0.3 | 0.1 |
| HLA- | 0.2 | 0.278 | 0.3 | 0.2 | 0.2 | 0.352 | 0.5 | 0.2 | 0.2 | 0.300 | 0.1 | 0.2 |
| HLA- | 0.6 | 0.577 | 0.5 | 0.6 | 0.5 | 0.511 | 0.5 | 0.4 | 0.5 | 0.522 | 0.5 | 0.4 |
| HLA- | 0.5 | 0.613 | 1.0 | 0.5 | 0.0 | 0.136 | 0.1 | 0.0 | 0.0 | 0.000 | 0.0 | 0.0 |
| HLA- | 0.0 | 0.319 | 0.1 | 0.0 | 0.2 | 0.246 | 0.5 | 0.2 | 0.0 | 0.100 | 0.0 | 0.0 |
| HLA- | 0.0 | 0.441 | 0.2 | 0.0 | 0.0 | 0.482 | 0.2 | 0.0 | 0.0 | 0.403 | 0.1 | 0.0 |
| HLA- | 0.0 | 0.115 | 0.0 | 0.0 | 0.0 | 0.000 | 0.0 | 0.0 | 0.0 | 0.117 | 0.0 | 0.0 |
| HLA- | 0.2 | 0.332 | 1.0 | 0.2 | 0.1 | 0.161 | 0.3 | 0.1 | 0.2 | 0.146 | 0.1 | 0.1 |
| HLA- | 0.2 | 0.304 | 0.3 | 0.2 | 0.2 | 0.168 | 0.2 | 0.2 | 0.0 | 0.226 | 0.1 | 0.0 |
| HLA- | 0.0 | 0.000 | 0.0 | 0.0 | 0.0 | 0.000 | 0.0 | 0.0 | 0.1 | 0.275 | 1.0 | 0.1 |
| HLA- | 0.1 | 0.137 | 0.3 | 0.1 | 0.0 | 0.000 | 0.0 | 0.0 | 0.1 | 0.137 | 0.3 | 0.1 |
| HLA- | 0.0 | 0.060 | 0.0 | 0.0 | 0.1 | 0.185 | 0.2 | 0.1 | 0.2 | 0.306 | 0.3 | 0.2 |
| HLA- | 1.0 | 1.000 | 1.0 | 1.0 | 0.5 | 0.387 | 0.5 | 0.5 | 0.0 | 0.000 | 0.0 | 0.0 |
| HLA- | 0.1 | 0.108 | 0.1 | 0.1 | 0.0 | 0.000 | 0.0 | 0.0 | 0.0 | 0.095 | 0.1 | 0.0 |
| HLA- | 0.0 | 0.280 | 0.1 | 0.0 | 0.3 | 0.358 | 0.3 | 0.3 | 0.0 | 0.302 | 0.2 | 0.0 |
| HLA- | 0.0 | 0.000 | 0.0 | 0.0 | 0.0 | 0.000 | 0.0 | 0.0 | 0.0 | 0.000 | 0.0 | 0.0 |
| HLA- | 0.4 | 0.894 | 1.0 | 0.4 | 0.2 | 0.335 | 0.5 | 0.2 | 0.4 | 0.550 | 1.0 | 0.4 |
| HLA- | 0.1 | 0.151 | 0.3 | 0.1 | 0.1 | 0.303 | 1.0 | 0.1 | 0.0 | 0.143 | 0.1 | 0.0 |
| HLA- | 1.0 | 1.000 | 1.0 | 1.0 | 1.0 | 1.000 | 1.0 | 1.0 | 1.0 | 1.000 | 1.0 | 1.0 |
| HLA- | 0.2 | 0.318 | 0.3 | 0.2 | 0.2 | 0.296 | 0.2 | 0.2 | 0.1 | 0.183 | 0.2 | 0.1 |
| HLA- | 0.0 | 0.042 | 0.0 | 0.0 | 0.0 | 0.096 | 0.1 | 0.0 | 0.0 | 0.046 | 0.0 | 0.0 |
| HLA- | 0.1 | 0.222 | 1.0 | 0.1 | 0.2 | 0.180 | 0.3 | 0.1 | 0.1 | 0.125 | 0.1 | 0.1 |
| HLA- | 0.0 | 0.338 | 0.2 | 0.0 | 0.3 | 0.343 | 0.3 | 0.3 | 0.0 | 0.287 | 0.1 | 0.0 |

TABLE 2-continued

Performance comparison per allele, between the best predictor described herein and
MHCflurry-2.0 baseline, the proposed immunogenicity benchmark. Reported metrics are:
Precision@K (P@K), nDCG20, Reciprocal Rank (RR) and Positive Predictive Value (PPV),
in all higher is better.

| | BigMHC-2.0 | | | | BigMHC-1.3 | | | | MHCflurry-2.0 | | | |
|---|---|---|---|---|---|---|---|---|---|---|---|---|
| Allele | P@K | $nDCG_{20}$ | RR | PPV | P@K | $nDCG_{20}$ | RR | PPV | P@K | $nDCG_{20}$ | RR | PPV |
| HLA- | 0.0 | 0.000 | 0.0 | 0.0 | 0.0 | 0.000 | 0.0 | 0.0 | 0.0 | 0.000 | 0.0 | 0.0 |
| HLA- | 0.2 | 0.214 | 0.5 | 0.2 | 0.2 | 0.214 | 0.5 | 0.2 | 0.2 | 0.214 | 0.5 | 0.2 |
| HLA- | 0.2 | 0.390 | 1.0 | 0.2 | 0.2 | 0.344 | 0.5 | 0.2 | 0.0 | 0.139 | 0.1 | 0.0 |

REFERENCES CITED IN THE EXAMPLES

1. Vita, R.; Mahajan, S.; Overton, J. A.; Dhanda, S. K.; Martini, S.; Cantrell, J. R.; Wheeler, D. K.; Sette, A.; Peters, B. The immune epitope database (IEDB): 2018 update. Nucleic acids research 2019, 47, D339-D343.
2. Kim, Y.; Sidney, J.; Buus, S.; Sette, A.; Nielsen, M.; Peters, B. Dataset size and composition impact the reliability of performance benchmarks for peptide-MHC binding predictions. BMC bioinformatics 2014, 15, 241.
3. O'Donnell, T. J.; Rubinsteyn, A.; Bonsack, M.; Riemer, A. B.; Laserson, U.; Hammerbacher, J. MHCflurry: open-source class I MHC binding affinity prediction. Cell systems 2018, 7, 129-132. 4. Sarkizova, S.; Klaeger, S.; Le, P. M.; Li, L. W.; Oliveira, G.; Keshishian, H.; Hartigan, C. R.; Zhang, W.; Braun,
D. A.; Ligon, K. L.; others. A large peptidome dataset improves HLA class I epitope prediction across most of the human population. Nature Biotechnology 2020, 38, 199-209.
5. Shao, W.; Pedrioli, P. G.; Wolski, W.; Scurtescu, C.; Schmid, E.; Vizcaíno, J. A.; Courcelles, M.; Schuster, H.; Kowalewski, D.; Marino, F.; others. The SysteMHC atlas project. Nucleic acids research 2018, 46, D1237-D1247.
6. Abelin, J. G.; Harjanto, D.; Malloy, M.; Suri, P.; Colson, T.; Goulding, S. P.; Creech, A. L.; Serrano, L. R.; Nasir, G.; Nasrullah, Y.; others. Defining HLA-II ligand processing and binding rules with mass spectrometry enhances cancer epitope prediction. Immunity 2019, 51, 766-779.
7. Sidney, J.; Peters, B.; Frahm, N.; Brander, C.; Sette, A. HLA class I supertypes: a revised and updated classification. BMC immunology 2008, 9, 1.
8. O'Donnell, T.; Rubinsteyn, A.; Laserson, U. Improved predictive models for peptide presentation on MHC I. BioRxiv 2020.
9. Consortium, U. UniProt: a worldwide hub of protein knowledge. Nucleic acids research 2019, 47, D506-D515.
10. Lin, T. Y.; Goyal, P.; Girshick, R.; He, K.; Dollár, P. Focal loss for dense object detection. Proceedings of the IEEE international conference on computer vision, 2017, pp. 2980-2988.
11. Mukhoti, J.; Kulharia, V.; Sanyal, A.; Golodetz, S.; Torr, P. H.; Dokania, P. K. Calibrating Deep Neural Networks using Focal Loss. arXiv preprint arXiv: 2002.09437 2020.
12. Guo, C.; Pleiss, G.; Sun, Y.; Weinberger, K. Q. On calibration of modern neural networks. arXiv preprint arXiv: 1706.04599 2017.
13. O'Donnell, T. J.; Rubinsteyn, A.; Laserson, U. MHCflurry 2.0: Improved Pan-Allele Prediction of MHC Class I-Presented Peptides by Incorporating Antigen Processing. Cell Systems 2020.
14. Fischer, W.; Perkins, S.; Theiler, J.; Bhattacharya, T.; Yusim, K.; Funkhouser, R.; Kuiken, C.; Haynes, B.; Letvin, N. L.; Walker, B. D.; others. Polyvalent vaccines for optimal coverage of potential T-cell epitopes in global HIV-1 variants. Nature medicine 2007, 13, 100-106.
15. Jurtz, V.; Paul, S.; Andreatta, M.; Marcatili, P.; Peters, B.; Nielsen, M. NetMHCpan-4.0: improved peptide-MHC class I interaction predictions integrating eluted ligand and peptide binding affinity data. The Journal of Immunology 2017, 199, 3360-3368.
16. Consortium, U. UniProt: a worldwide hub of protein knowledge. Nucleic acids research 2019, 47, D506-D515.

6. EQUIVILANTS

It will be readily apparent to those skilled in the art that other suitable modifications and adaptions of the methods of the invention described herein are obvious and may be made using suitable equivalents without departing from the scope of the disclosure or the embodiments. Having now described certain compositions and methods in detail, the same will be more clearly understood by reference to the following examples, which are introduced for illustration only and not intended to be limiting.

What is claimed is:

1. A method for predicting tumor-specific neoantigen MHC class I immunogenicity, comprising:
   a) obtaining a peptide sequence for a tumor-specific neoantigen and the corresponding flanking regions of the peptide sequence; encoding the peptide sequence and the flanking regions into a numerical vector, wherein each numerical vector comprises amino acid residues encoding the peptide for the tumor-specific neoantigen and the amino acid residues of the flanking regions and the amino acid residue position;
   b) obtaining a HLA allele pseudo-sequence, wherein the HLA allele pseudo-sequence represents a HLA allele; encoding the HLA allele sequence into a corresponding numerical vector;
   c) using a neural network model to jointly predict the tumor-specific neoantigen MHC class I binding affinity and a numerical probability for each tumor-specific neoantigen that a corresponding peptide will be presented by a MHC class I protein on a cell-surface; wherein using the neural network model comprises the steps of:
      (i) training the neural network model on a training data set to optimize performance of the neural network model; wherein the training data set comprises peptide-MHC class I affinity measurement data sets and cell-surface peptide presentation data sets and an input layer comprising the numerical vector comprising the peptide sequence for the tumor-specific neoantigen and the flanking regions and the numerical vector comprising the HLA allele pseudo-sequence layer;

(ii) encoding the numerical vector comprising the peptide sequence for the tumor-specific neoantigen and the flanking regions and the numerical vector comprising the HLA allele pseudo-sequence into an amino acid embedding layer;

(iii) flattening the amino acid embedding layer to produce a numerical vector representation for each peptide sequence for the tumor-specific neoantigen and the peptide sequence flanking regions, and HLA allele pseudo-sequence;

(iv) predicting the tumor-specific neoantigen MHC class I binding affinity by concatenating the tumor-specific neoantigen peptide sequence and the HLA allele pseudo-sequence, applying one or more layers and/or one or more activation functions, wherein the output is a numerical score representing the tumor-specific neoantigen MHC class I binding affinity; and (v) predicting a probability that the tumor-specific neoantigen will be presented by a MHC class I protein on a cell-surface by concatenating the peptide sequence of interest, the peptide sequence flanking regions, and the HLA allele pseudo-sequence into a single numerical vector, applying one or more layers and/or one or more activation functions, wherein an output is a numerical probability that a peptide will be presented by a MHC class I protein on a cell-surface;

wherein the tumor-specific neoantigen MHC class I binding affinity and the numerical probability that the tumor-specific neoantigen will be presented by a MHC class I protein on a cell-surface is a proxy for tumor-specific neoantigen MHC class I immunogenicity.

2. The method of claim 1, further comprising validating the neural network model by:

(i) applying one or more ranking metrics to an immunogenicity validation data set;

(ii) ranking peptides for each allele in the immunogenicity validation data set based on the peptide's predicted MHC class I binding affinity and the numerical probability that a peptide will be presented by a MHC class I protein on a cell-surface; and (iii) aggregating the one or more ranking metrics for all alleles.

3. The method of claim 2, wherein the one or more ranking metrics is aggregated by using weighted allele frequencies.

4. The method of claim 1, wherein the neural network model is a pan-allele model, an allele-specific model, a super-type specific model, or a combination thereof.

5. The method of claim 1, wherein the HLA allele pseudo-sequence is about 30 amino acids to about 60 amino acids in length.

6. The method of claim 1, wherein the peptide sequence for a tumor-specific neoantigen is about 8 amino acids in length to about 15 amino acids in length.

7. The method of claim 1, wherein the flanking region is directly left of the tumor-specific neoantigen peptide sequence and/or directly right of the tumor-specific neoantigen peptide sequence.

8. The method of claim 1, wherein the flanking region is about 10 amino acids in length.

9. The method of claim 8, wherein the flanking region directly left of the tumor-specific neoantigen is about 5 amino acids in length.

10. The method of claim 8, wherein the flanking region directly right of the tumor-specific neoantigen is about 5 amino acids in length.

11. The method of claim 1, further comprising calibrating the neural network model.

12. The method of claim 1, wherein the neural network model is trained on positive training data and negative training data.

13. The method of claim 12, wherein negative training data comprises peptides that do not have tumor-specific neoantigen MHC class I binding affinity and/or are not presented by a MHC class I protein on a cell-surface.

14. The method of claim 1, wherein the HLA-allele is HLA type A, B, or C.

15. The method of claim 1, wherein the tumor-specific neoantigen MHC class I immunogenicity is CD8+ T-cell immunogenicity.

16. The method of claim 1, wherein one or more tumor-specific neoantigens predicted to be MHC class I immunogenic are selected for an immunogenic composition.

17. The method of claim 16, wherein at least about 20 tumor-specific neoantigens are selected for the immunogenic composition.

18. The method of claim 1, wherein the one or more layers is a fully connected layer or a dropout layer.

19. The method of claim 1, wherein the one or more layers and/or activation function comprises applying one or more fully-connected layers, applying a dropout layer, and applying an activation function.

20. The method of claim 11, wherein the neural network model is calibrated with a probabilistic computation.

21. The method of claim 11, wherein the probabilistic computation estimates the overall presentation probability for a subject's alleles.

* * * * *